(12) United States Patent
Chappell et al.

(10) Patent No.: US 7,985,568 B2
(45) Date of Patent: Jul. 26, 2011

(54) BOTRYOCCOCUS BRAUNII TRITERPENE SYNTHASE PROTEINS AND NUCLEIC ACID MOLECULES, AND METHODS FOR THEIR USE

(75) Inventors: Joe Chappell, Lexington, KY (US); Shigeru Okada, Tokyo (JP); Tom Niehaus, Lexington, KY (US); Tim Devarenne, Bryan, TX (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 12/539,442

(22) Filed: Aug. 11, 2009

(65) Prior Publication Data

US 2010/0041120 A1  Feb. 18, 2010

Related U.S. Application Data

(60) Provisional application No. 61/087,920, filed on Aug. 11, 2008.

(51) Int. Cl.
*C12P 5/00* (2006.01)

(52) U.S. Cl. .... 435/166; 435/69.1; 435/183; 435/320.1; 530/350; 530/300; 536/23.2

(58) Field of Classification Search ........................ None
See application file for complete search history.

(56) References Cited

OTHER PUBLICATIONS

Wells, Biochemistry, vol. 29, pp. 8509-8517, 1990.*
Seffernick et al. (J. Bacteriology, vol. 183, pp. 2405-2410, 2001).*
Blagg BSJ, Jarstfer MB, Rogers DH, Poulter CD (2002) Recombinant squalene synthase. A mechanism for the rearrangement of presqualene diphosphate to squalene. Journal of the American Chemical Society 124: 8846-8853.
Jarstfer MB, Zhang DL, Poulter CD (2002) Recombinant squalene synthase. Synthesis of non-head-to-tail isoprenoids in the absence of NADPH. Journal of the American Chemical Society 124: 8834-8845.
Poulter CD (1990) Biosynthesis of Non-Head-to-Tail Terpenes—Formation of 1'-1 and 1'-3 Linkages. Accounts of Chemical Research 23: 70-77.

* cited by examiner

*Primary Examiner* — Hope Robinson
(74) *Attorney, Agent, or Firm* — Crowell & Moring LLP

(57) ABSTRACT

This application relates to the functional identification and characterization of a nucleic acid molecule encoding a triterpene synthase, in particular botryococcene synthase. Also described are host cells comprising the nucleic acid molecules of this invention, proteins encoded by the nucleic acid molecules and methods for using the nucleic acid molecules, transformed hosts and encoded proteins to produce high levels of triterpene hydrocarbons.

6 Claims, 11 Drawing Sheets

```
ATGATGACTATGCACCAAGACCACGGAGTCATGAAAGACCTTGTCAAGCATCCAAATGAAT
TTCCATACTTGCTCCAACTAGCTGCAACATACGGCTCACCGGCTGCACCGATCCCCAAGGA
ACCGGACCGAGCTTTCTGCTACAATACTCTTCACACCGTTTCGAAGGGGTTCCCCTTTGTT
ATGAGACTTCCGCAGGAACTCCAAGATCCGATATGCATATTCTACCTCCTGTTGCGAGCAC
TAGACACGGTGGAGGATGATATGAACCTCAAAAGTGAGACGAAGATTTCACTCCTACGCGT
TTTCCATGAACACTGTTCAGACAGGAACTGGAGTATGAAAAGTGATTATGGCATATATGCA
GATCTGATGGAAAGATTCCCCCTGGTCGTATCCGTCTTAGAGAAGCTCCCTCCCGCCACAC
AGCAGACTTTCAGGGAGAATGTCAAATACATGGGCAATGGCATGGCAGATTTTATTGATAA
GCAGATCCTGACAGTGGATGAGTACGACCTCTACTGCCACTATGTGGCCGGCAGTTGCGGC
ATTGCTGTCACCAAGGTCATTGTGCAGTTCAACCTTGCCACGCCTGAAGCTGACTCCTACG
ACTTTTCCAACAGTCTGGGCCTCTTGCTTCAGAAGGCCAACATCATCACTGACTACAATGA
AGACATCAATGAAGAGCCCAGGCCCAGGATGTTCTGGCCCCAGGAGATTTGGGGGAAGTAC
GCGGAGAAGTTGGCTGACTTCAATGAACCCGAAAATATTGATACAGCCGTGAAGTGCTTGA
ACCACATGGTCACAGATGCAATGCGGCACATTGAGCCTTCCCTCAAAGGCATGGTTTATTT
CACAGACAAGACAGTCTTTCGGGCGCTCGCTCTTCTGCTGGTCACAGCCTTTGGCCATTTG
TCCACTTTGTACAACAACCCCAATGTCTTTAAAGAGAAAGTGAGACAGCGGAAGGGAAGGA
TTGCACGGCTGGTCATGTCATCCAGGAATGTACCAGGCCTCTTCCGTACATGCCTCAAACT
CGCAAACAACTTCGAGTCCAGGTGCAAGCAAGAGACGGCAAATGATCCCACTGTGGCCATG
ACTATCAAGCGCTTGCAATCTATTCAAGCTACATGCAGAGATGGCCTGGCCAAGTATGACA
CACCCTCTGGGCTGAAATCTTTCTGCGCAGCCCCAACTCCCACCAAGTGA
```

FIG. 4

```
MTMHQDHGVMKDLVKHPNEFPYLLQLAATYGSPAAPIPKEPDRAFCYNTLHTVSKGFPFVM
RLPQELQDPICIFYLLLRALDTVEDDMNLKSETKISLLRVFHEHCSDRNWSMKSDYGIYAD
LMERFPLVVSVLEKLPPATQQTFRENVKYMGNGMADFIDKQILTVDEYDLYCHYVAGSCGI
AVTKVIVQFNLATPEADSYDFSNSLGLLLQKANIITDYNEDINEEPRPRMFWPQEIWGKYA
EKLADFNEPENIDTAVKCLNHMVTDAMRHIEPSLKGMVYFTDKTVFRALALLLVTAFGHLS
TLYNNPNVFKEKVRQRKGRIARLVMSSRNVPGLFRTCLKLANNFESRCKQETANDPTVAMT
IKRLQSIQATCRDGLAKYDTPSGLKSFCAAPTPTK
```

BOTRYOCCOCUS BRAUNII TRITERPENE SYNTHASE PROTEINS AND NUCLEIC ACID MOLECULES, AND METHODS FOR THEIR USE

CLAIM TO PRIORITY

This application claims priority under 35 U.S.C. 119(e) to U.S. provisional application No. 61/087,920 filed Aug. 11, 2008, incorporated in its entirety by reference.

SEQUENCE LISTING

The instant application contains a Sequence Listing which has been submitted via EFS-Web and is hereby incorporated by reference in its entirety. Said ASCII copy, created on Oct. 12, 2009, is named 14726673.txt, and is 14,577 bytes in size.

FIELD OF THE INVENTION

This invention relates to a triterpene synthase, in particular a botryococcene synthase, proteins and nucleic acid molecules and their use.

BACKGROUND OF THE INVENTION

Squalene and botryococcene are related by their putative biosynthetic origins from the condensation of two farnesyl diphosphate (FPP) molecules, and are known to be synthesized by race B, a fresh water green algae (Okada.et al., (1995). *Journal Of Applied Phycology* 555-559.; Metzger and Largeau (2005). *Applied Microbiology and Biotechnology* 486-496.) Botryococcene is further modified in and becomes methylated with 1, 2, 3 or 4 additional methyl substituents catalyzed by a special triterpene methyl transferase. Botryococcene and its methylated derivatives have attracted significant attention because these molecules are thought to be the progenitors to current oil shale deposits (Summons et al., (2002) *Organic Geochemistry* 99-109; Walters et al., (2005) *Aapg Bulletin* 1239-1 244.) and because they are considered promising renewable, alternative biofuels (Banerjee et al., (2002). *Critical Reviews in Biotechnology* 245-279.) For example, Hillen et al. (1982) *Biotechnology And Bioengineering* 193-205) previously reported on the catalytic cracking of methylated botryococcenes and squalene derivatives, and observed an overall conversion of 97% of the oil to combustible fuels under standard cracking conditions. Overall, 67% of the oil was converted to gasoline grade fuel, 15% to aviation turbine fuel, and 15% to diesel fuel with a residual of only 3%. Hence, catalytic hydrolysis (as performed in standard petroleum refineries) of these highly branched, poly-unsaturated triterpenes results in the generation of hydrocarbon fractions that are chemically equivalent to those derived from current petroleum deposits and are of direct utility as fuels for internal combustion engines, as well as feedstocks for chemical manufacturing (Banerjee et al., (2002)).

Up to this time, these energy-rich triterpene oils have only been available from cultures of a rather slow growing green algae that does not lend itself to large-scale or fermentation type culturing conditions (Casadevall et al., (1985). *Biotechnology and Bioengineering* 286-295).

BRIEF DESCRIPTION OF THE INVENTION

The current disclosure describes the functional identification and characterization of the gene coding for a triterpene synthase in particular a botryococcene synthase, BBS, enzyme. The identification of the botryococcene synthase gene now provides an alternative means of generating important raw materials for the reliable and cost effective production of an energy-rich, renewable, and sustainable biofuel source (FIG. 3). For example, the co-expression of the botryococcene synthase gene in combination with a suitable FPP synthase and triterpene methyltransferase genes in transgenic terrestrial or aquatic plants could yield a production platform for the methylated triterpenes. These compounds could be derived from the metabolic diversion of $CO_2$ fixed in the process of photosynthesis flowing directly into triterpene biosynthesis and accumulation. The feasibility of this engineering strategy for the production of large amounts of high-valued sesquiterpenes, terpenes consisting of 15 carbons rather than the 30 carbons found in triterpenes, was recently demonstrated. (Wu et al., (2006) *Nature Biotechnology* 14411447).

The botryococcene synthase of this invention is a triterpene synthase enzyme catalyzing the reductive condensation of 2 farnesyl diphosphate (FPP) substrate molecules yielding botryococcene, a 30-carbon, branched-chain hydrocarbon.

More specifically, disclosed herein is the DNA and protein sequence of, and the functional characterization for, the race B botryococcene synthase gene which, when expressed in a heterologous host such as bacteria, yeast or plants yields a protein that, when mixed with a lysate and reducing equivalents in the form of NADPH, provides an enzyme activity that catalyzes a unique chemical condensation of 2 FPP molecules, creating a branched, triterpene hydrocarbon known as botryococcene. A schematic diagram of the reaction catalyzed by the botryococcene synthase enzyme is shown in FIG. 1. Like squalene synthase (Blagg et al., (2002) *J. Am. Chem. Soc.* 8846-8853), botryococcene synthase is predicted to catalyze a 2 step reaction. The first step condenses the 2 FPP substrate molecules into a pre-squalene diphosphate intermediate (PSPP). When NADPH is provided, squalene synthase reduces the PSPP to a linkage of carbons 1 and 1' of the respective FPP molecules. In contrast, when botryococcene synthase is provided NADPH, the PSPP undergoes a different reducing rearrangement to botryococcene with a linkage of carbon 3 of one FPP starter molecule to carbon 1' of the second FPP starter molecule.

BRIEF DESCRIPTION OF THE DRAWINGS

FIG. 4 presents the DNA sequence for the botryococcene synthase cDNA, SEQ ID NO: 1. The start and stop codons are shown in bold.

FIG. 5 presents the amino acid sequence for the botryococcene synthase protein, SEQ ID NO: 2, predicted from the corresponding cDNA sequence shown in FIG. 4.

DETAILED DESCRIPTION OF THE INVENTION

Figure 1:
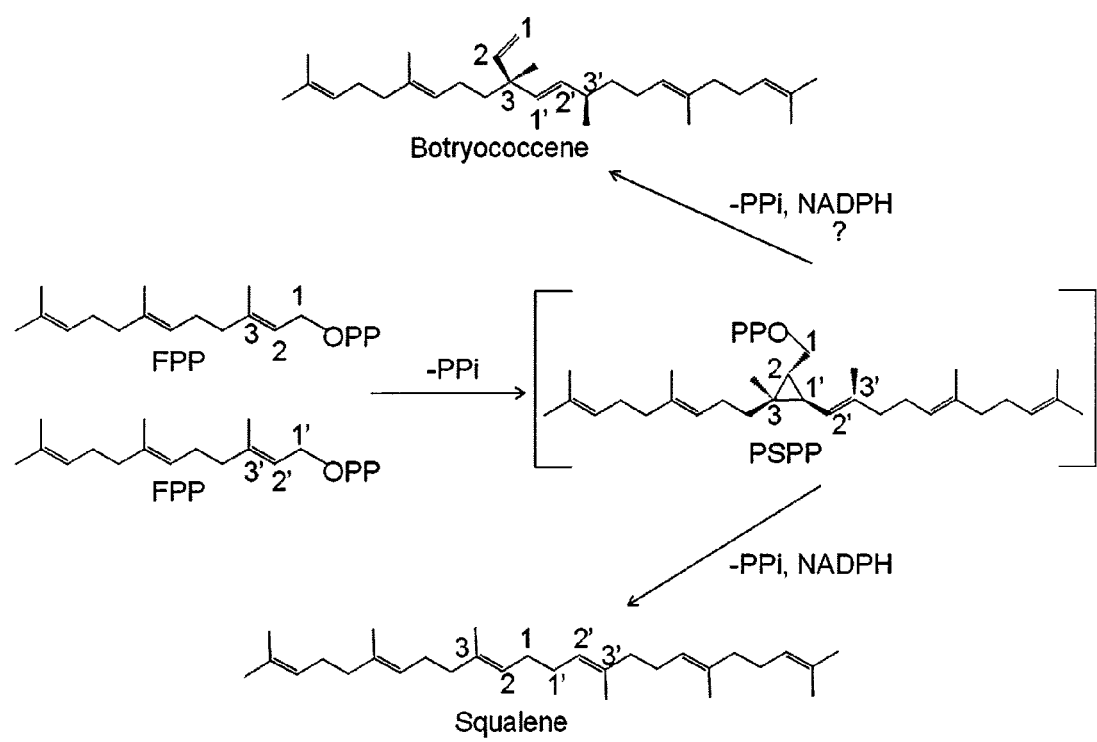
FIG. 1 depicts the biosynthetic pathways for botryococcene and squalene. Both triterpenes are derived from an initial condensation of 2 FPP molecules to form presqualene diphosphate (PSPP), which is subsequently cleaved and reduced to form either botryococcene or squalene.
Figure 2:
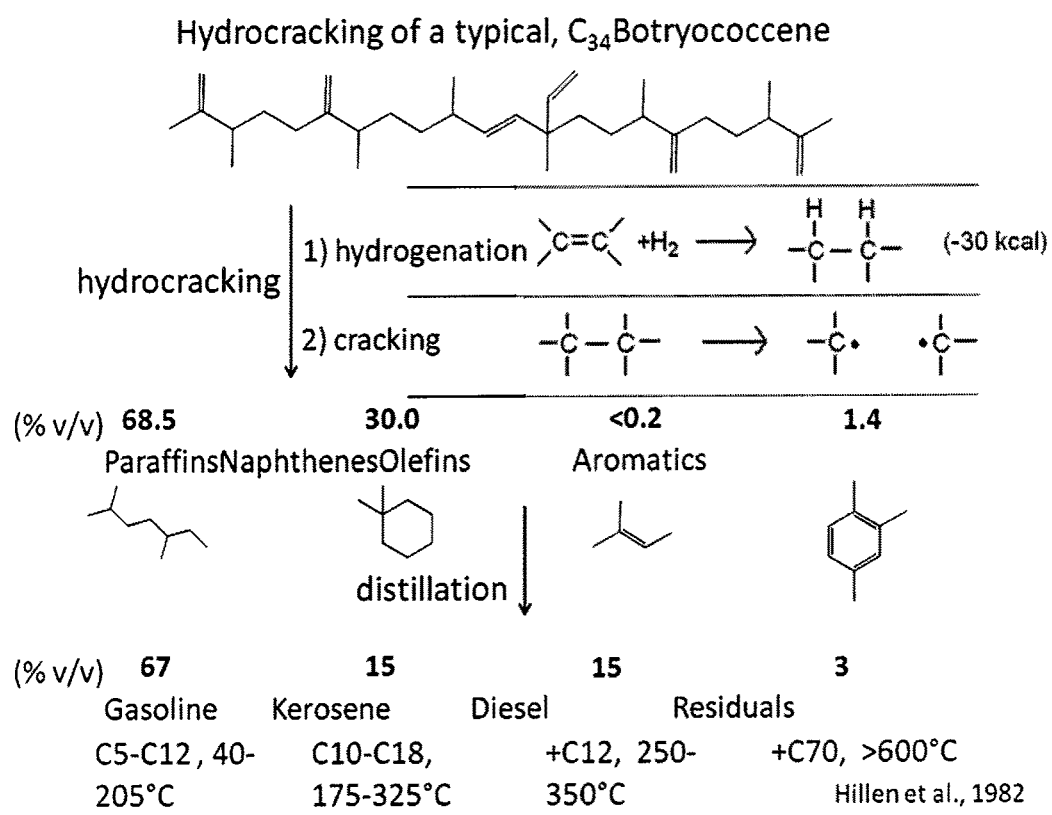
FIG. 2 depicts an overview of the hydrocracking process of a typical, $C_{34}$ botryococcene to yield fuel suitable for combustion engines. Briefly, botryococcenes are treated with high pressure $H_2$ at high temperatures with a Pd catalyst to give a variety of organic molecules, which can be further distilled into various classes of fuel.
Figure 3:
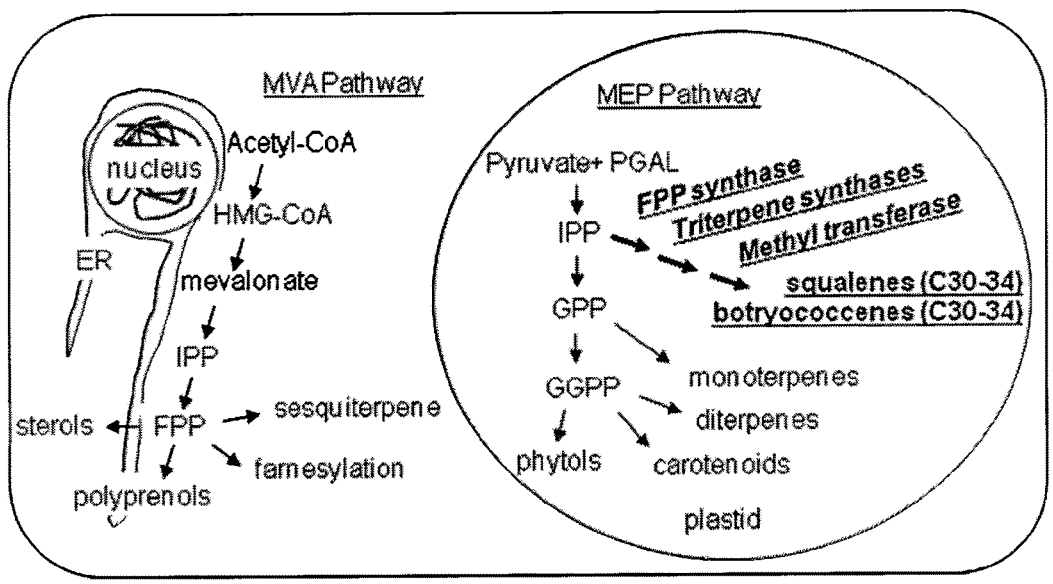
FIG. 3 depicts a strategy for engineering an alternative biofuels production platform into terrestrial or aquatic plants. Genes coding for the biochemical steps for synthesis of botryococcenes would be introduced into plants such that the respective catalytic steps (FPP synthase, triterpene synthase and triterpene methyltransferase activities) would be targeted to the chloroplast compartment. The introduced enzyme activities would hence divert photosynthetically fixed $CO_2$ directly into methylated triterpene biosynthesis.

The current disclosure describes the functional identification and characterization of the gene coding for a botryococcene synthase, BBS, enzyme, nucleic acid molecules e.g. SEQ ID NO: 1, encoding a botryococcene synthase, BBS, polypeptide of this invention, e.g., SEQ ID NO: 2 and methods for their use.

The polypeptides of this invention include for example polypeptides comprising the amino acid sequence set forth in SEQ ID NO:2 and fragments thereof. Preferably the polypeptide fragments have triterpene synthase activity. The polypeptides of this invention may comprise one or more peptide domains I, II, III, IV, V and IV, wherein domain I comprises LPQELQDPICIFYL (SEQ ID NO: 3.), domain II comprises LRALDTVEDDMN LKSETK (SEQ ID NO; 4), domain III comprises YCHYVAGSCGIAV TKVIV (SEQ ID NO: 5), domain IV comprises GLLLQKANIITD YNED (SEQ ID NO 6), and domain V comprises ALALLLVTAFGHLS (SEQ ID NO: 7).

The polypeptides of this invention may also contain one or more modified amino acids. The presence of modified amino acids may be advantageous in, for example, increasing triterpene synthase catalytic activity or increasing polypeptide stability. Amino acid(s) are modified, for example, co-translationally or post-translationally during recombinant production (e.g., N-linked glycosylation at N—X—S/T motifs during expression in mammalian cells) or modified by synthetic means. Accordingly, a "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises because of degeneracy of the genetic code wherein more than one codon codes for the same amino acid.

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

Recombinant methods for producing and isolating the triterpene synthase polypeptides and modified triterpene synthase polypeptides of the invention are described herein. In addition to recombinant production, the polypeptides may be produced by direct peptide synthesis using solid-phase techniques (e.g., Stewart et al. (1969) Solid-Phase Peptide Synthesis (WH Freeman Co, San Francisco); and Merrifield (1963) *J. Am. Chem. Soc.* 85: 2149-2154; each of which is incorporated by reference). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer.

A "protein" or "polypeptide", which terms are used interchangeably herein, comprises one or more chains of chemical building blocks called amino acids that are linked together by chemical bonds called peptide bonds. An "enzyme" means any substance, composed wholly or largely of protein, that catalyzes or promotes, more or less specifically, one or more chemical or biochemical reactions. A "native" or "wild-type" protein, enzyme, polynucleotide, gene, or cell, means a protein, enzyme, polynucleotide, gene, or cell that occurs in nature (whose form predominates in natural populations).

Accordingly, in various embodiments, isolated or recombinant polypeptides comprising the amino acid sequence set forth in SEQ ID NO:2 are provided. The polypeptides include up to 35, 25, 10, 5, 4, 3, 2 or 1 conservative amino acid substitutions.

"Conservative amino acid substitutions" or, simply, "conservative variations" of a particular sequence refers to the replacement of one amino acid, or series of amino acids, with essentially identical amino acid or series of amino acids. One of skill will recognize that individual substitutions, deletions or additions which alter, add or delete a single amino acid or a percentage of amino acids in an encoded sequence result in "conservative variations" where the alterations result in the deletion of an amino acid, addition of an amino acid, or substitution of an amino acid with a functionally similar amino acid.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a listed polypeptide sequence (e.g., SEQ ID NO:2) include substitutions of a percentage, typically less than 10%, of the amino acids of the polypeptide sequence, with an amino acid of the same conservative substitution group. Accordingly, a conservatively substituted variation of a polypeptide of the invention can contain, for example, substitutions of 35, 25, 10, 5, 4, 3, 2 or 1 amino acid with an amino acid of the same conservative substitution group.

It is understood that the addition of sequences that do not alter the encoded activity of a nucleic acid molecule, such as the addition of a non-functional or non-coding sequence, is a conservative variation of the basic nucleic acid molecule. The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. As used interchangeably herein a "triterpene synthase activity", "biological activity of triterpene synthase" or "functional activity of triterpene synthase", refers to an activity exerted by a triterpene synthase protein, polypeptide or nucleic acid molecule on a triterpene synthase polypeptide substrate, as determined in vivo, or in vitro, according to standard techniques.

One of skill in the art will appreciate that many conservative substitutions of the nucleic acid constructs which are disclosed herein yield a functionally identical construct. For example, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid.

Similarly, "conservative amino acid substitutions," in which one or a few amino acids in an amino acid sequence are substituted with different amino acids with highly similar properties, are also readily identified as being highly similar to a disclosed construct. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such conservative variations of each disclosed sequence are a feature of the polypeptides provided herein.

It will be appreciated by those skilled in the art that due to the degeneracy of the genetic code, a multitude of nucleotide sequences encoding modified triterpene synthase polypeptides of the invention may be produced, some of which bear substantial identity to the nucleic acid sequences explicitly disclosed herein. For instance, codons AGA, AGG, CGA, CGC, CGG, and CGU all encode the amino acid arginine. Thus, at every position in the nucleic acid molecules of the invention where an arginine is specified by a codon, the codon can be altered to any of the corresponding codons described above without altering the encoded polypeptide. It is understood that U in an RNA sequence corresponds to T in a DNA sequence.

"Conservative variants" are proteins or enzymes in which a given amino acid residue has been changed without altering overall conformation and function of the protein or enzyme, including, but not limited to, replacement of an amino acid with one having similar properties, including polar or nonpolar character, size, shape and charge. Amino acids other than those indicated as conserved may differ in a protein or enzyme so that the percent protein or amino acid sequence similarity between any two proteins of similar function may vary and can be, for example, at least 30%, at least 50%, at least 70%, at least 80%, at least 90%, at least 95%, at least 98% or at least 99%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, (1985) *Science* 22; 227(4693):1435-41; Pearson and Lipman, (1988) *Proc Natl Acad Sci USA;* 85(8):2444-8). When using all of these programs, the preferred settings are those that results in the highest sequence similarity.

Non-conservative modifications of a particular polypeptide are those which substitute any amino acid not characterized as a conservative substitution. For example, any substitution which crosses the bounds of the six groups set forth above. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic amino acids include lysine (K), arginine (R), histidine (H); acidic amino acids include aspartic acid (D), glutamic acid (E); uncharged polar amino acids include glycine (G), asparagine (N), glutamine (Q), serine (S), threonine (T), tyrosine (Y), cysteine (C); nonpolar amino acids include alanine (A), valine (V), leucine (L), isoleucine (I), proline (P), phenylalanine (F), methionine (M), tryptophan (W); beta-branched amino acids include threonine (T), valine (V), isoleucine (I); aromatic amino acids include tyrosine (Y), phenylalanine (F), tryptophan (W), histidine (H).

A polynucleotide, polypeptide, or other component is "isolated" when it is partially or completely separated from components with which it is normally associated (other proteins, nucleic acid molecules, cells, synthetic reagents, etc.). A nucleic acid molecule or polypeptide is "recombinant" when it is artificial or engineered, or derived from an artificial or engineered protein or nucleic acid molecule. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant. For example, an "isolated" nucleic acid molecule is one which is separated from other nucleic acid molecules which are present in the natural source of the nucleic acid molecule. For example, with regards to genomic DNA, the term "isolated" includes nucleic acid molecules which are separated from the chromosome with which the genomic DNA is naturally associated. Typically, an "isolated" nucleic acid molecule is free of sequences which naturally flank the nucleic acid molecule (i.e., sequences located at the 5' and 3' ends of the nucleic acid molecule) in the genomic DNA of the organism from which the nucleic acid molecule is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid molecule is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

In some embodiments, a polypeptide provided herein includes amino acid residue substitutions that correspond to positions in a particular sequence at least 80%, 85%, 90%, 95%, 98% or 99% of the time. In other words, the invention encompasses polypeptides that contain the recited amino acid substitutions at 80%, 85%, 90%, 95%, 98% or 99% of the recited positions in a given sequence. The skilled artisan will recognize that not every substitution from a group of substitutions is necessary to obtain a modified polypeptide that is active on a triterpene substrate.

"Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, (1985), Pearson and Lipman, (1988)). When using all of these programs, the preferred settings are those that results in the highest sequence similarity. For example, the "identity" or "percent identity" with respect to a particular pair of aligned amino acid sequences can refer to the percent amino acid sequence identity that is obtained by ClustalW analysis (version W 1.8 available from European Bioinformatics Institute, Cambridge, UK), counting the number of identical matches in the alignment and dividing such number of identical matches by the greater of (i) the length of the aligned sequences, and (ii) 96, and using the following default ClustalW parameters to achieve slow/accurate pairwise alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins" in "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) *Proc. Nat'l. Acad. Sci. USA* 89: 10915-10919 (each of which is incorporated by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucl. Acids Res.* 25: 3389-3402 (incorporated by reference herein), and made available to the public at the National Center for Biotechnology Information (NCBI) Website (www.ncbi.nlm.nih.gov). Optimal alignments, including multiple alignments, can be prepared using, e.g., PSI-BLAST, available through the NCB1 website and described by Altschul et al. (1997) Nucl. Acids Res. 25:3389-3402 (incorporated by reference herein).

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. For example, in SEQ ID NO:2, position 1 is M, position 2 is T, position 3 is M, etc. When a test sequence is optimally aligned with SEQ ID NO:2, a residue in the test sequence that aligns with the M at position 3 is said to "correspond to position 3" of SEQ ID NO:2. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Also contemplated are fragments of the full length triterpene synthase polypeptides and polynucleotides, e.g., fragments of polypeptides comprising the amino acid sequence set forth in SEQ ID NO: 2 and fragments of nucleic acid molecules comprising the sequence set forth in SEQ ID NO: 1. A "fragment" is a unique portion of a triterpene synthase polypeptide or the polynucleotide encoding triterpene synthase which is identical in sequence to, but shorter in length than, the parent sequence. A fragment may comprise up to the entire length of the defined sequence, minus one nucleotide/ amino acid residue. For example, a fragment may comprise from 5 to 1000 contiguous nucleotides or amino acid residues of a given nucleic acid molecule or polypeptide. A fragment used as a probe, primer, antigen, catalytic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

Also contemplated in this invention are isolated polypeptides that are triterpene synthases, that comprise 5 peptide domains I, II, III, IV, and V. The peptide domains I, II, III, IV, and V of the triterpene synthase of this invention may comprise respectively, e.g., SEQ ID NO: 3, SEQ ID NO: 4, SEQ ID NO: 5, SEQ ID NO: 6, and SEQ ID NO: 7 (See FIG. 6, the 5 domains of *B. braunii* (BBS)). In an embodiment of the invention, domain I comprises an amino acid sequence that is at least 20%, 30%, 40%, 50%, 60%, 70%, 80%, 90% or 95% identical to the full-length of SEQ ID NO: 3, domain II comprises an amino acid sequence that is at least 20%, 30%, 40%, 50%, 60%, 70%, 80%, 90% or 95% identical the full-length of SEQ ID NO: 4, domain III may comprise an amino acid sequence that is at least 20%, 30%, 40%, 50%, 60%, 70%, 80%, 90% or 95% identical to the full-length of SEQ ID NO: 5, domain IV comprises an amino acid sequence that is at least 20%, 30%, 40%, 50%, 60%, 70%, 80%, 90% or 95% identical to the full-length of SEQ ID NO: 6 and domain V comprises an amino acid sequence that is at least 20%, 30%, 40%, 50%, 60%, 70%, 80%, 90% or 95% identical the full-length of SEQ ID NO: 7. The 5 peptide domains may be present in the synthase in any order, preferably the order of the 5 peptides in the polypeptide is, from its amino to carboxy terminal, I, II, III, IV, and V, and more preferably the I, II, III, IV and V domains comprise respectively SEQ ID NO: 3, SEQ ID NO: 4, SEQ ID NO: 5, SEQ ID NO: 6 and SEQ ID NO: 7.

In other embodiments, isolated nucleic acid molecules are provided. Described herein are nucleic acid molecules that encode a polypeptide having triterpene synthase activity, in particular a *Botryococcus braunii* triterpene synthase. The nucleic acid molecules of this invention include e.g., nucleic acid molecules that encode the amino acid sequence set forth in SEQ ID NO: 2, nucleic acid molecules that encode fragments of SEQ ID NO: 2, nucleic acid molecules that comprise SEQ ID NO:1, and nucleic acid molecules that encode fragments of SEQ ID NO: 1. In one aspect, the invention provides a novel family of isolated or recombinant polynucleotides referred to herein as "triterpene synthase polynucleotides" or "triterpene synthase nucleic acid molecules." Triterpene synthase polynucleotide sequences are characterized by the ability to encode a triterpene synthase polypeptide. In general, the invention includes any nucleotide sequence that encodes any of the novel triterpene synthase polypeptides described herein. The terms "polynucleotide," "nucleotide sequence," and "nucleic acid molecule" are used to refer to a polymer of nucleotides (A, C, T, U, G, etc. or naturally occurring or artificial nucleotide analogues), e.g., DNA or RNA, or a representation thereof, e.g., a character string, etc., depending on the relevant context. A given polynucleotide or complementary polynucleotide can be determined from any specified nucleotide sequence.

In an aspect, the triterpene synthase polynucleotides comprise recombinant or isolated forms of naturally occurring nucleic acid molecules isolated from an organism, e.g., an algae strain. Exemplary triterpene synthase polynucleotides include those that encode the polypeptide set forth in SEQ ID NO:2. In another aspect of the invention, triterpene synthase polynucleotides are produced by diversifying, e.g., mutating, a naturally occurring, isolated, or recombinant triterpene synthase polynucleotide, e.g., the nucleic acid sequence set forth in SEQ ID NO: 1. It is possible to generate diversified triterpene synthase polynucleotides encoding triterpene synthase polypeptides with superior functional attributes, e.g., increased catalytic function, increased stability, or higher expression level, than a triterpene synthase encoded by the polynucleotide used as a substrate or parent in the diversification process.

The polynucleotides of the invention have a variety of uses in, for example recombinant production (i.e., expression) of the triterpene synthase polypeptides of the invention and as substrates for further diversity generation, e.g., recombination reactions or mutation reactions to produce new and/or improved triterpene synthase homologues, and the like.

It is important to note that certain specific, substantial and credible utilities of triterpene synthase polynucleotides do not require that the polynucleotide encode a polypeptide with substantial triterpene synthase activity or even variant triterpene synthase activity. For example, triterpene synthase polynucleotides that do not encode active enzymes can be valuable sources of parental polynucleotides for use in diversification procedures to arrive at triterpene synthase polynucleotide variants, or non-triterpene synthase polynucleotides, with desirable functional properties (e.g., high $k_{cat}$ or $k_{cat}/K_m$, low $K_m$, high stability towards heat or other environmental factors, high transcription or translation rates, resistance to proteolytic cleavage, etc.).

Triterpene synthase polynucleotides, including nucleotide sequences that encode triterpene synthase polypeptides and variants thereof, fragments of triterpene synthase polypeptides, related fusion proteins, or functional equivalents thereof, are used in recombinant DNA molecules that direct the expression of the triterpene synthase polypeptides in appropriate host cells, such as plant cells. Due to the inherent degeneracy of the genetic code, other nucleic acid sequences which encode substantially the same or a functionally equivalent amino acid sequence can also be used to clone and express the triterpene synthase polynucleotides. The term "host cell", as used herein, includes any cell type which is susceptible to transformation with a nucleic acid construct. The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang et al. (1991) *Gene* 105:61-72; incorporated by reference herein). Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) *Nucl. Acids Res.* 17:477-508; incorporated by reference herein) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA, respectively. The preferred stop codon for monocotyledonous plants is UGA, whereas insects and *E. coli* prefer to use UAA as the stop codon (Dalphin et al. (1996) *Nucl. Acids Res.* 24: 216-218; incorporated by reference herein). Methodology for optimizing a nucleotide sequence for expression in a plant is provided, for example, in U.S. Pat. No. 6,015,891, and the references cited therein (incorporated herein by reference).

"Silent variations" are one species of "conservative substitutions." One of skill will recognize that each codon in a nucleic acid sequence (except AUG, which is ordinarily the only codon for methionine) can be modified by standard techniques to encode a functionally identical polypeptide. Accordingly, each silent variation of a nucleic acid sequence that encodes a polypeptide is implicit in any described sequence. The invention provides each and every possible variation of nucleic acid sequence encoding a polypeptide of the invention that could be made by selecting combinations based on possible codon choices. These combinations are made in accordance with the standard triplet genetic code as applied to the nucleic acid sequence encoding a triterpene synthase homologue polypeptide of the invention. All such variations of every nucleic acid sequence herein are specifically provided and described by consideration of the sequence in combination with the genetic code. Any variant can be produced as noted herein.

In general, the invention includes any polypeptide encoded by a modified triterpene synthase polynucleotide derived by mutation, recursive sequence recombination, and/or diversification of the polynucleotide sequences described herein. In some aspects of the invention, a triterpene synthase polypeptide is modified by single or multiple amino acid substitutions, a deletion, an insertion, or a combination of one or more of these types of modifications. Substitutions can be conservative or non-conservative, can alter function or not, and can add new function. Insertions and deletions can be substantial, such as the case of a truncation of a substantial fragment of the sequence, or in the fusion of additional sequence, either internally or at N or C terminal.

An aspect of the invention pertains to isolated nucleic acid molecules that encode modified triterpene synthase polypeptides or biologically active portions thereof. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule of the present invention, e.g., a nucleic acid molecule that encodes a polypeptide set forth in SEQ ID NO:2, or having the nucleotide sequence of set forth in SEQ ID NO:1, or a portion thereof, can be isolated using standard molecular biology techniques and the sequence information provided herein.

A nucleic acid molecule of the invention can be amplified using cDNA, mRNA or alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer. In some embodiments, an isolated nucleic acid molecule of the invention comprises a nucleic acid molecule which is a complement of a nucleotide sequence encoding a polypeptide set forth in SEQ ID NO:2, or complement of the nucleotide sequence set forth in SEQ ID NO:1. In still another embodiment, an isolated nucleic acid molecule of the invention comprises a nucleotide sequence which is at least about 50%, 52%, 55%, 60%, 62%, 65%, 70%, 75%, 78%, 80%, 85%, 88%, 90%, 95%, 97%, 98% or more identical to the nucleotide sequence encoding a polypeptide set forth in SEQ ID NO:2, or the nucleotide sequence set forth in SEQ ID NO:1, or a portion of any of these nucleotide sequences.

In addition to the nucleotide sequences encoding a polypeptide set forth in SEQ ID NO:2, or the nucleotide sequence set forth in SEQ ID NO:1, it will be appreciated by those skilled in the art that DNA sequence polymorphisms that lead to changes in the amino acid sequences of the proteins may exist within a population. Such genetic polymorphisms may exist among individuals within a population due to natural allelic variation. Such natural allelic variations include both functional and non-functional proteins and can typically result in 1-5% variance in the nucleotide sequence of a gene. Any and all such nucleotide variations and resulting amino acid polymorphisms in genes that are the result of natural allelic variation and that do not alter the functional activity of a protein are intended to be within the scope of the invention.

Accordingly, in another embodiment, an isolated nucleic acid molecule of the invention hybridizes under stringent conditions to a nucleic acid molecule comprising the nucleotide sequence encoding a polypeptide set forth in SEQ ID NO:2, or the nucleotide sequence set forth in SEQ ID NO:1. In other embodiments, the nucleic acid molecule is at least 30, 50, 100, 150, 200, 250, 300, 350, 400, 450, 500, 550, or 600 nucleotides in length. Nucleic acid molecules are "hybridizable" to each other when at least one strand of one polynucleotide can anneal to another polynucleotide under defined stringency conditions. Stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences (1×SSC is 0.15 M NaCl, 0.015 M Na citrate).

Nucleic acid molecules that hybridize include those which anneal under suitable stringency conditions and which encode polypeptides or enzymes having the same function, such as the ability to catalyze the reductive condensation of 2 farnexyl diphosphate (FPP) substrate molecules yielding botryococcene, a 30-carbon branched-chain hydrocarbon, of the invention. Further, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. In some cases, an isolated nucleic acid molecule of the invention that hybridizes under stringent conditions to a nucleic acid sequence encoding a polypeptide set forth in any of SEQ ID NO:2, or the nucleotide sequence set forth in SEQ ID NO:1, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). Preferably the nucleic acid molecule that hybridizes, hybridizes to at least 30%, 40%, 50%, 60%, 70%, 80%, 85% or 90% of the length of a nucleic acid molecule consisting of SEQ ID NO:1 under stringent conditions. More preferably the nucleic acid molecule that hybridizes, hybridizes to at least about 80%, even more preferably at least about 85% or 90% of the length of a nucleic acid molecule consisting of SEQ ID NO: 1. Preferably the nucleic acid molecule that hybridizes encodes a polypeptide having triterpene synthase activity.

The skilled artisan will appreciate that changes can be introduced by mutation into the nucleotide sequences of any nucleic acid sequence encoding a polypeptide set forth in SEQ ID NO:2, or having the nucleotide sequence set forth in SEQ ID NO:1, thereby leading to changes in the amino acid sequence of the encoded proteins. In some cases the alteration will lead to altered function of the polypeptide. In other cases the change will not alter the functional ability of the encoded polypeptide. In general, substitutions that do not alter the function of a polypeptide include nucleotide substitutions leading to amino acid substitutions at "non-essential" amino acid residues. Generally these substitutions can be made in, for example, the sequence encoding a polypeptide set forth in SEQ ID NO:2, or having the nucleotide sequence set forth in SEQ ID NO:1, without altering the ability of the enzyme to catalyze the reductive condensation of FPP substrate. A "non-essential" amino acid residue is a residue that can be altered from the parent sequence without altering the biological activity of the resulting polypeptide, e.g., catalyzing the reductive condensation of 2 FPP to yield botryococcene.

Also contemplated are those situations where it is desirable to alter the activity of a parent polypeptide such that the polypeptide has new or increased activity on a particular substrate. It is understood that these amino acid substitutions will generally not constitute "conservative" substitutions. Instead, these substitutions constitute non-conservative substitutions introduced in to a sequence in order to obtain a new or improved activity.

It is also understood that an isolated nucleic acid molecule encoding a polypeptide homologous to the polypeptide of SEQ ID NO:2 can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the nucleic acid sequence by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions.

Mutational methods of generating diversity include, for example, site-directed mutagenesis (Ling et al. (1997) *Anal Brioche.* 254(2): 157-178; Dale et al. (1996) *Methods Mol. Biol.* 57:369-374; Smith (1985) *Ann. Rev. Genet.* 19:423-462; Botstein & Shortle (1985) *Science* 229:1193-1201; Carter (1986) *Biochem. J.* 237:1-7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)); mutagenesis using uracil containing templates (Kunkel (1985) *Proc. Natl. Acad. Sci. USA* 82:488-492; Kunkel et al. (1987) *Methods in Enzymol.* 154, 367-382; and Bass et al. (1988) *Science* 242:240-245); oligonucleotide-directed mutagenesis (*Methods in Enzymol.* 100: 468-500 (1983); *Methods in Enzymol.* 154: 329-350 (1987); Zoller & Smith (1982) *Nucleic Acids Res.* 10:6487-6500; Zoller & Smith (1983) *Methods in Enzymol.* 100:468-500; and Zoller & Smith (1987) *Methods in Enzymol.* 154:329-350); phosphorothioate-modified DNA mutagenesis (Taylor et al. (1985) *Nucl. Acids Res.* 13: 8749-8764; Taylor et al. (1985) *Nucl. Acids Res.* 13: 8765-8787; Nakamaye & Eckstein (1986) *Nucl. Acids Res.* 14: 9679-9698; Sayers et al. (1988) *Nucl. Acids Res.* 16:791-802; and Sayers et al. (1988) *Nucl. Acids Res.* 16: 803-814); mutagenesis using gapped duplex DNA (Kramer et al. (1984) *Nucl. Acids Res.* 12: 9441-9456; Kramer & Fritz (1987) *Methods in Enzymol.* 154:350-367; Kramer et al. (1988) *Nucl. Acids Res.* 16: 7207; and Fritz et al. (1988) *Nucl. Acids Res.* 16: 6987-6999) (each of which is incorporated by reference).

Additional suitable methods include point mismatch repair (Kramer et al. (1984) *Cell* 38:879-887), mutagenesis using repair-deficient host strains (Carter et al. (1985) *Nucl. Acids Res.* 13: 4431-4443; and Carter (1987) *Methods in Enzymol.* 154: 382-403), deletion mutagenesis (Eghtedarzadeh & Henikoff (1986) *Nucl. Acids Res.* 14: 5115), restriction-selection and restriction-purification (Wells et al. (1986) *Phil. Trans. R. Soc. Lond.* A 317: 415-423), mutagenesis by total gene synthesis (Nambiar et al. (1984) *Science* 223: 1299-1301; Sakamar and Khorana (1988) *Nucl. Acids Res.* 14: 6361-6372; Wells et al. (1985) *Gene* 34:315-323; and Grundstrom et al. (1985) *Nucl. Acids Res.* 13: 3305-3316); double-strand break repair (Mandecki (1986); Arnold (1993) *Current Opinion in Biotechnology* 4:450-455; and *Proc. Natl. Acad. Sci. USA,* 83:7177-7181) (each of which is incorporated by reference). Additional details on many of the above methods can be found in *Methods in Enzymology* (1987) Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997); U.S. Pat. No. 5,811,238 to Stemmer et al. (Sep. 22, 1998); U.S. Pat. No. 5,830,721 to Stemmer et al. (Nov. 3, 1998); U.S. Pat. No. 5,834,252 to Stemmer, et al. (Nov. 10, 1998); U.S. Pat. No. 5,837,458 to Minshull, et al. (Nov. 17, 1998); WO 95/22625, Stemmer and Crameri; WO 96/33207 by Stemmer and Lipschutz; WO 97/20078 by Stemmer and Crameri; WO 97/35966 by Minshull and Stemmer; WO 99/41402 by Punnonen et al.; WO 99/41383 by Punnonen et al.; WO 99/41369 by Punnonen et al.; WO 99/41368 by Punnonen et al.; EP 752008 by Stemmer and Crameri; EP 0932670 by Stemmer; WO 99/23107 by Stemmer et al.; WO 99/21979 by Apt et al.; WO 98/31837 by del Cardayre et al.; WO 98/27230 by Patten and Stemmer; WO 98/13487 by Stemmer et al.; WO 00/00632; WO 00/09679; WO 98/42832 by Arnold et al.; WO 99/29902 by Arnold et al.; WO 98/41653 by Vind; WO 98/41622 by Borchert et al.; WO 98/42727 by Pati and Zarling; WO 00/18906 by Patten et al.; WO 00/04190 by del Cardayre et al.; WO 00/42561 by Crameri et al.; WO 00/42559 by Selifonov and Stemmer; WO 00/42560 by Selifonov et al.; WO 01/23401 by Welch et al.; and WO 01/64864 by Affholter (each of which is incorporated by reference). The QUICKCHANGE™ protocol marketed by Stratagene of San Diego, Calif. is one specific method known to those skilled in the art for introducing site-directed mutations. This method relies on the use of oligo or DNA primer pairs, harboring specific DNA sequence changes to be introduced, annealed to the target DNA or gene to be modified. Copies of modified DNA/gene are amplified by standard PCR methodology. Confirmation of alteration of the target DNA sequence is verifiable by automated DNA sequencing.

Also provided are recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences including, for example, a promoter operably linked to the sequence. Large numbers of suitable vectors and promoters are known to those of skill in the art, and are commercially available.

Accordingly, in other embodiments, vectors that include a nucleic acid molecule of the invention are provided.

In other embodiments, host cells transfected with a nucleic acid molecule of the invention, or a vector that includes a nucleic acid molecule of the invention, are provided. Host cells include eukaryotic cells such as yeast cells, e.g., yeast cells having a ERG1 knockout, e.g., the yeast strain TN7 described in co-pending application Ser. No. 12/489,038 incorporated herein in its entirety, insect cells, animal cells, or plant cells (e.g., algal cells or terrestrial plant cells). Host cells also include procaryotic cells such as bacterial cells.

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and viral vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), pMAL plasmids (New England Biolabs, Beverly, Mass.), and Ti plasmid vectors, and many appropriate host cells, using methods disclosed or cited herein or otherwise known to those skilled in the relevant art. Vectors can also be selected such that expression of the introduced sequence is targeted to a chloroplast in a plant cell. Recombinant cloning vectors will often include one or more replication systems for cloning or expression, one or more markers for selection in the host, e.g., antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Polynucleotides provided herein can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses; Ti plasmids for the incorporation and expression of DNA in plant cells, and many others. Any vector that transduces genetic material into a cell, and, if replication is desired, which is replicable and viable in the relevant host can be used.

Vectors can be employed to transform an appropriate host to permit the host to express an inventive protein or polypeptide. Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 br Bowes melanoma; plant cells e.g., *Nicotiana tabacum*, a dicot plant species, or corn, a monocot plant species; algal cells e.g., *Chlamydomonas reinhardtii*; or explants of any plant tissues, e.g., leaf, stem or root segments, etc.

In bacterial systems, a number of expression vectors may be selected depending upon the use intended for the triterpene synthase polypeptide. For example, when large quantities of triterpene synthase polypeptide or fragments thereof are needed for commercial production or for induction of antibodies, vectors which direct high level expression of fusion proteins that are readily purified can be desirable. Such vectors include, but are not limited to, multifunctional *E. coli* cloning and expression vectors such as BLUESCRIPT™ (Stratagene), in which the triterpene synthase polypeptide coding sequence may be ligated into the vector in-frame with sequences for the amino-terminal Met and the subsequent 7 residues of 6-galactosidase so that a hybrid protein is produced; pIN vectors (Van Heeke & Schuster (1989) J. Biol. Chem. 264: 5503-5509); pET vectors (Novagen, Madison Wis.); and the like.

Similarly, in the yeast *Saccharomyces cerevisiae* a number of vectors containing constitutive or inducible promoters isolated from, e.g., an alpha factor, an alcohol dehydrogenase or a PGH gene may be used for production of the triterpene synthase polypeptides of the invention. For reviews, see Ausubel (supra) and Grant et al. (1987) *Methods in Enzymology* 153:516-544 (incorporated herein by reference).

Plant and algal systems may also be used for expression of triterpene synthase. Transcription of sequences encoding triterpene synthase may be driven by viral promoters, e.g., the 35S and 19S promoters of CaMV used alone or in combination with the omega leader sequence from TMV (Takamatsu, N. (1987) *EMBO J.* 6:307-311). Alternatively, plant promoters such as, e.g., the small subunit of RUBISCO or heat shock promoters may be used. (See, e.g., Coruzzi, G. et al. (1984) EMBO J. 3:1671-1680; Broglie, R. et al. (1984) *Science* 224:838-843; and Winter, J. et al. (1991) *Results Probl. Cell Differ.* 17:85-105.) For algal expression work, a strong constitutive promoter includes, e.g., a F-tubulin gene promoter (see Brunke, K J et al. (1984) *Molec. Cell. Biol.* 4: 1115-1124). These constructs can be introduced into plant cells, for example, by direct DNA transformation or pathogen-mediated transfection. (See, e.g., The McGraw Bill Yearbook of Science and Technology (1992) McGraw Hill, New York N.Y., pp. 191-196.)

Also provided are engineered host cells that are transduced (transformed or transfected) with a vector provided herein (e.g., a cloning vector or an expression vector), as well as the production of polypeptides of the invention by recombinant techniques. The vector may be, for example, a plasmid, a viral particle, a phage, etc. The engineered host cells can be cultured in conventional nutrient media modified as appropriate for activating promoters, selecting transformants, or amplifying the triterpene synthase gene. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York) and the references cited therein.

In other embodiments, methods for producing a cell that catalyzes a unique chemical condensation of 2 FPP molecules creating a branched, triterpene hydrocarbon, botryococcene, are provided. Such methods generally include: (a) transforming a host cell with an isolated nucleic acid molecule encoding a triterpene synthase polypeptide, e.g., a nucleic acid molecule encoding a polypeptide comprising SEQ ID NO: 2, a variant, preferably a conservative variant, of SEQ ID NO: 2, or a fragment of SEQ ID NO: 2 having triterpene synthase activity and (b) culturing the transformed cell to produce the botryococcene. For example a transformed yeast cell of this invention may be cultured by large scale fermentation, providing the added advantage of producing large amounts of triterpenes, particularly botryococcene.

In other embodiments, methods for selecting a cell that converts 2 FPP to botryococcene are provided. The methods generally include: (a) providing a host cell containing a nucleic acid construct that includes a nucleotide sequence that encodes a triterpene synthase polypeptide. The methods further include (b) culturing the cell in the presence of a suitable 2 FPP and under conditions where the triterpene synthase is expressed at an effective level; and (c) detecting the production of botryococcene.

In other embodiments, methods for producing botryococcene are provided. In one aspect, the methods for producing a botryococcene comprise culturing a host cell transfected with a nucleic acid molecule that encodes a triterpene synthase, preferably a triterpene synthase of this invention under conditions sufficient for production of a botryococcene. Optionally, the botryococcene produced by the host cells are isolated. The host cell may be, for example, a cell in culture, e.g., the yeast strain TN7 transfected with a vector of this invention, or it may be a cell which is part of an organism such as a transfected cell in a terrestrial plant. In addition to transfection with triterpene synthase-encoding nucleic acid molecule, such plant cells may also be cotransfected with nucleic acid molecules encoding for one or more other enzymes in the triterpene synthesis pathway, such as the genes for farnesyl diphosphate synthase or a triterpene synthase such as squalene synthase or triterpene methyltransferase. Plant cells for transfection include, for example algal cells such as *Botryococcus* spp. cells (e.g., *Botryococcus braunii*), *Chlamydomonas* spp. cells or terrestrial plant cells, such as a tobacco plant cell. Transfection of plant cells with exogenous genes may be directed to the cytosolic compartment, the chloroplast or both. In other embodiments, cells other than plant cells may be transformed with triterpene synthase-encoding nucleic acid molecules, and optionally with nucleic acid molecules encoding one or more other enzymes involved in triterpene synthesis. These cells include, for example, prokaryotic cells such as bacteria and eukaryotic cells, such as fungi or animal cells. In particular the cells may be a natural or recombinant yeast cells, e.g., yeast cells that accumulate FPP but do not metabolize squalene, e.g., yeast cells with a mutant or deleted or disrupted EGR1 gene such that it produces reduced or no squalene epoxidase, e.g., a yeast strain such as TN7. In any of the aforementioned embodiments, the cells may also be genetically altered to enhance the production of farnesyl diphosphate and thereby provide a larger precursor pool for triterpene synthesis, such as through gene knockout, so as to eliminate or reduce diversion of farnesyl diphosphate for use in synthesis of metabolites other than triterpenes, such as sesquiterpenes, sterols, or polyprenols, or to eliminate or reduce the action of phosphatase(s) on farnesyl diphosphate.

The production of triterpenes may also be enhanced by diverting other metabolic intermediates such as, e.g., isopentenyl diphosphate or dimethylallyl diphosphate (DMAPP) to the production of FPP, therein providing enhanced carbon flux to a key intermediate for the biosynthesis of triterpenes.

Also an aspect of this invention is a method for producing triterpenes comprising transfecting a yeast strain having high intracellular concentrations of FPP and reduced levels of squalene epoxidase with a nucleic acid molecule encoding a triterpene synthase and culturing the transfected cells under conditions suitable for the production of triterpenes. The triterpene synthase may be, e.g., a botryococcene synthase or a squalene synthase. The botryococcene synthase may be, e.g., a botryococcene synthase of this invention, e.g., a botryococcene synthase comprising the amino acid sequence of SEQ ID NO:2 or a conservative variant thereof, or a fragment thereof having botryococcene synthase activity. The high intracellular concentrations of FPP may be, e.g., at least 10 mg/L, at least 20 mg/L, at least 30 mg/L, at least 40 mg/L, at least 50 mg/L, at least 60 mg/L, at least 70 mg/L, or at least 80 mg/L. The reduced squalene epoxidase may be, e.g., less than the levels of squalene epoxidase found in the yeast strain CALI-7 (Takahashi et al., (2007) "Metabolic Engineering of Sesquiterpene Metabolism in Yeast" Biotech. Bioeng. 170-181). The reduced squalene expoxidase levels may also be undetectable levels, such as the levels in the yeast strain TN7.

In another aspect, cells transfected with a nucleic acid molecule encoding a triterpene synthase are cultured under conditions suitable for the expression of the triterpene synthase polypeptide and an extract rich in triterpene synthase is then prepared. This extract may be, for example, a cell paste or tissue homogenate, or it may be, for example, a purified or partially purified preparation of triterpene synthase. FPP, e.g., radiolabelled FPP, plus or minus reducing equivalents (NaDPH) and algal lysates is then exposed to the extract rich in triterpene synthase under conditions which allow for production of botryococcene. The reductive condensation may be via a batch process or a continuous process. Optionally the botryococcene may then be isolated.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel") (each of which is incorporated by reference). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem. 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564 (each of which is incorporated by reference). Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein (incorporated by reference herein), in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

These and other embodiments of the present invention will readily occur to those of ordinary skill in the art in view of the disclosure herein, and are specifically contemplated.

The invention is further understood by reference to the examples set forth herein, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

EXAMPLES

Example 1

Isolation of the *Botryococcus braunii* Botryococcene Synthase Gene

A cDNA library was constructed from mRNA isolated from cells in rapid growth phase, corresponding to 9 days after subculturing, converted to double stranded cDNAs, and the cDNAs inserted into the lambda ZAP™ vector (Stratagene, La Jolla, Calif.) as previously described by Okada et al. (2000) "Molecular characterization of squalene synthase from the green microalga *Botryococcus braunii*, race B". Archives Of Biochemistry and Biophysics 307-317. Plaque lifts of the cDNA library were prepared and hybridized with an 32PdCTP-radiolabeled full-length squalene synthase cDNA probe (referred to as SS1386 because it is 1386 bp long) using the Prime-It™ kit (Stratagene) at 30° C. in hybridization buffer consisting of 5× SSPE, 2× Denhardt's solution, 0.2% SDS, 100 g/ml salmon sperm DNA and 40% formamide, also according to Okada et al. (2000). The plaque lifts were then washed three times at room temperature for 5 min with 2×SSC, 0.1% SDS and hybridization detected by autoradiography. After 2 rounds of plaque purification, isolated plaques were converted to their plasmid forms following the procedures recommended by the manufacturer (Stratagene), and restriction digestions of the isolated plasmids compared. Those plasmids exhibiting restriction patterns similar to that for the squalene synthase were discarded and only those showing distinctive differences examined further by automated DNA sequencing (ABI 310 genetic analyzer, PE applied Biosystems, Foster City, Calif.).

DNA sequence of the entire botryococcene synthase (BBS) cDNA clone (FIG. 4) yielded a putative full-length cDNA clone coding for a 402 amino acid protein having a predicted molecular size of 45,692 daltons as shown in FIG.

Figure 6:
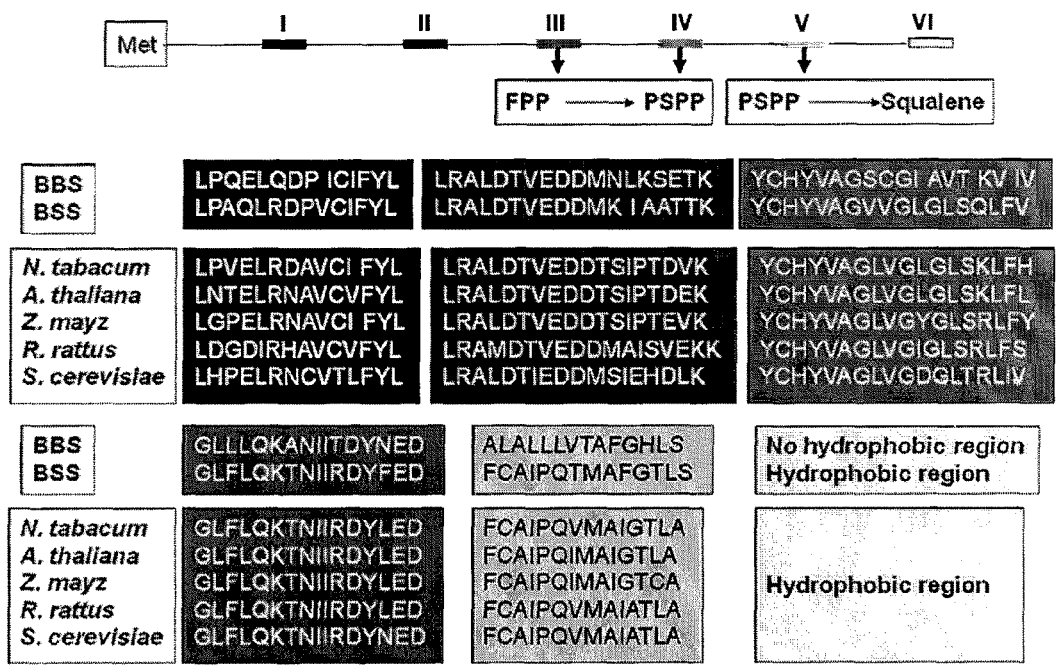
FIG. 6 depicts an alignment comparison of selection regions/domains of various squalene synthase proteins from *Botryococcus*(BSS), tobacco (*N. tabacum*), *Arabidopsis* (*A. thaliana*), corn (*Z. [[maize]]mays*), rat (*R. rattus*) and yeast (*S. cerevisiae*) to that for the botryococcene synthase (BBS). Domains I-VI were identified as highly conserved amongst diverse squalene synthases, and domains III-V were previously correlated with the particular steps in catalysis as noted. Sequences displayed across the 5 domains are: BBS, SEQ ID NO: 3, 4, 5, 6, and 7; BSS, SEQ ID NO: 8, 9, 10, 11, and 12; *N. tabacum* SEQ ID NO: 13, 14, 15, 16, and 17; *A. thaliana*, SEQ ID NO: 18, 19, 20, 21, and 22; *Z. [[maize]]mays*, SEQ ID NO: 23, 24, 25, 26 and 27; *R. rattus*, SEQ ID NO: 28, 29, 30, 31, ans 32; and *S. cerevisiae* SEQ ID NO: 33, 34, 35, 36 and 37.

5. Alignment of the predicted amino acid sequence from the BBS cDNA to other well described squalene synthase proteins from plants, animals and microbes demonstrated that there were several highly conserved domains shared between the predicted BBS protein and the various squalene synthases, but also there were several regions highly conserved amongst the various squalene synthases not found in the BBS protein (FIG. 6). Several of the domains conserved between BBS and the squalene synthases have been associated with early steps in the squalene synthase enzymatic reactions (domains I-IV), while domain V, associated with the conversion of PSPP to squalene, and a membrane-spanning domain (domain VI) are not conserved in the BBS protein.

Example 2

Functional Characterization of the Botryococcene Synthase Enzyme

The entire open reading frame, ORF, region of the BBS cDNA was amplified using standard RT-PCR conditions with a forward primer (5' CCCGCCACACAGCAGACTTTCAGGG 3' SEQ ID NO: 38, a reverse primer (5' CCTGGATGACATGACCAGCCGTGC 3' SEQ ID NO: 39 (designed according to the DNA sequence obtained from the initial BBS cDNA isolated from the cDNA library) and first strand cDNA as template. First strand cDNA was prepared from RNA isolated from rapidly growing cells via the Triazol method according the manufacturer's instructions (Invitrogen, Carlsbad, Calif.), and converted to single-strand DNA using oligo-dT primer and reverse transcriptase (Okada et al. 2000). The PCR amplification product was subsequently cloned in the pGEM T-Easy vector (Promega, Madison, Wis.) and the resulting recombinant plasmid subjected to automated DNA sequencing. The BBS cDNA was then PCR amplified from the pGEM vector using various primer combinations for the insertion of the BBS cDNA into bacterial expression vectors and into yeast expression vectors. To create bacterial expression vectors, a forward-primer (5' TTGGCGCCTATGACTATGCACCAAGACCACGG SEQ ID NO: 40) harboring an AscI restriction site reverse-(in bold) and primer (5' GGGGGCGCCTCACTTGGTGGGAGTTGGGGCTGCGC SEQ ID NO: 41) containing an XhoI restriction site (in bold) to PCR amplify the intact BBS cDNA from the pGEM vector and the amplified DNA ligated into the AscI and XhoI sites of a modified pET28b vector (Novagen, Madison Wis.) This vector was modified to contain an AscI restriction site 3' to the transcriptional elements within the vector. In order to generate a BBS protein with a hexa-histidine (SEQ ID NO: 44) amino-terminal extension, the full-length BBS cDNA was released from the pET28b vector by digestion with BamHI and XhoI, and the isolated fragment ligated into the corresponding sites of the pET28a vector. The pET28a expression vector is designed to include a DNA sequence coding for a hexa-histidine (SEQ ID NO: 44) amino acid extension fused in-frame with the amino terminus of the BBS cDNA, creating a fusion protein that facilitates nickel affinity purification of the bacterial expressed BBS protein The recombinant pET28a vector was transformed into E. coli strain BL21(DE3) according to the manufacturer's recommendations (Novagen) and the engineered bacteria were selected for growth in the presence of a suitable antibiotic selection marker.

E. coli harboring the recombinant plasmid were grown in liquid LB broth at 37° C. with vigorous shaking until the cultures reached an optical density of ~0.8 (OD nm), then expression of the BBS cDNA was induced by addition of 0.1 mM isopropylthio-B-D-galactoside (IPTG) and the cultures allowed to incubate for an additional 5 to 20 hours with shaking at room temperature. One hundred ml of the culture were subsequently collected by centrifugation at 4,000 g for 10 min, resuspended in 10 ml of lysis buffer (50 mM Tris-HCl, 2 mM MgCl$_2$ mM β-mercaptoethanol, 1 mM EDTA, 5% (v/v) glycerol, pH 7.5), then sonicated 5 times for 20 seconds with a microprobe sonicator at 60% maximum power. The samples were cooled on ice for 2 min between sonication treatments. The sonicate was centrifuged at 16,000 g for 15 min at 4° C. and used either for purification of the hexa-histidine tagged (SEQ ID NO: 44) BBS enzyme or 5-20 µl of the supernatant (corresponding to 10-100 g of total soluble protein) used for the botryococcene synthase enzyme assays as described by Okada et al., (2004)*Arch. Biochem. Biophys.* 110-118.

Figure 7:
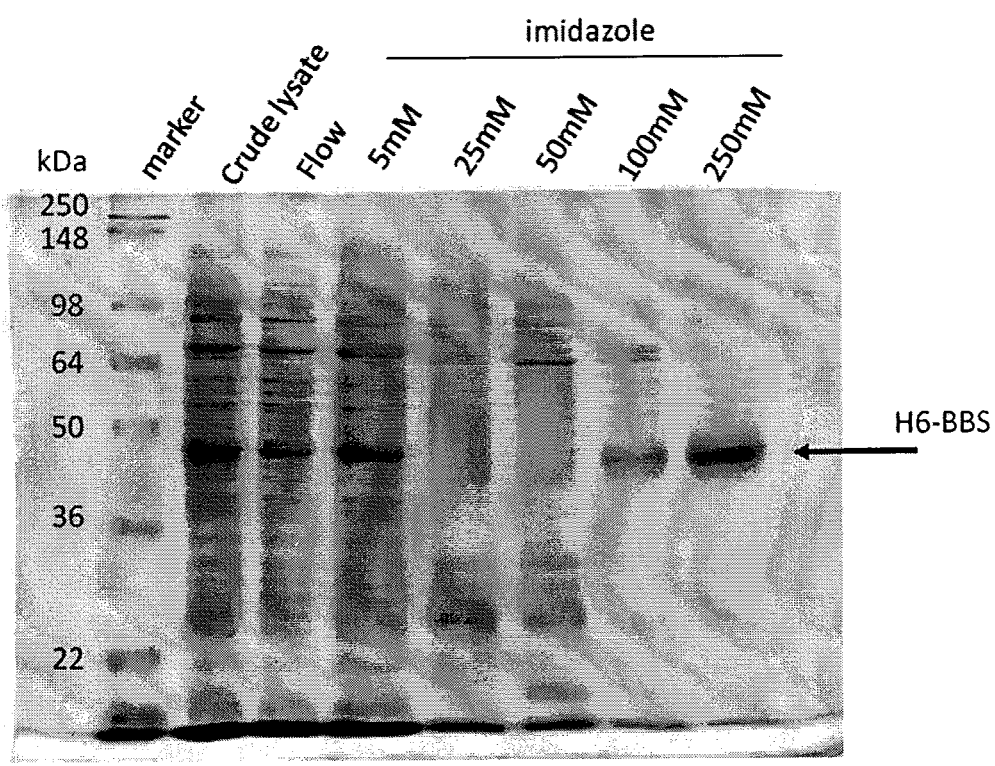
FIG. 7 depicts the purification of hexa-histidine tagged (SEQ ID NO: 44) BBS enzyme. *E. coli* cells over-expressing the botryococcene synthase gene harboring an amino terminal hexa-histidine purification tag (SEQ ID NO: 44) were used to prepare an initial cell lysate (crude lysate), which was then subject to nickle affinity chromatography. The crude lysate was applied to the affinity column, followed by washing with buffer containing increasing concentrations of imidazole (flow (buffer without imidazole, to buffer containing 250 mM imidazole) and the respective column fractions collected for SDS-PAGE analysis. Aliquots of each fraction were resolved by SDS-PAGE and the gel stained with Coomassie Blue, a general protein stain. Molecular weight standards are noted as marker and the expected size for the his-tagged BBS protein is noted by the arrow.

Purification of the bacterial expressed BBS enzyme was afforded by the amino-terminal hexa-histidine tag (SEQ ID NO: 44) using standard nickel affinity chromatography. In brief, aliquots of the bacterial lysate were applied to activated nickel columns according the manufacturer's recommendations (Novagen) and non-associating proteins eluted from the column using wash buffer. Selective elution of the hexa-histidine (SEQ ID NO: 44) BBS enzyme was observed at increasing concentrations of the counter ion, imidazole, with maximum recovery of protein at 250 mM imidazole and recovery of protein with the expected molecular size of 49,000 daltons (FIG. 7). Lysate prepared from bacteria over-expressing the BBS cDNA was prepared, applied to a nickel affinity column, and then proteins eluted with increasing concentrations of imidazole. Aliquots of the eluded fractions were examined by SDS-PAGE and stained with Coommassie Blue. Bradford dye analysis indicated that the protein content in the 250 mM imidazole fraction was 0.2 mg/ml.

Figure 8:
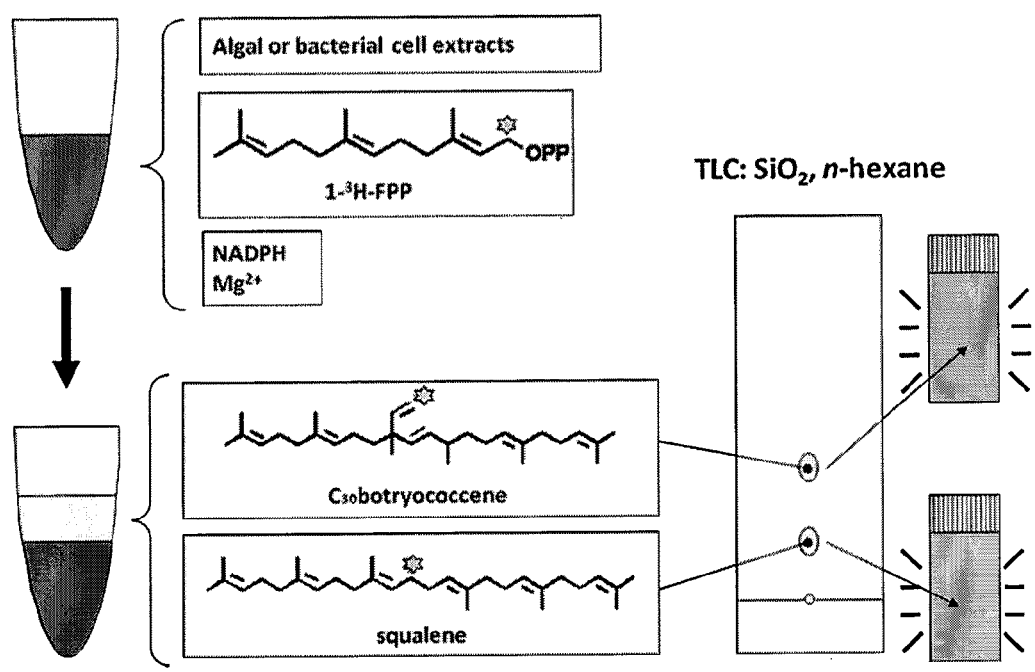
FIG. 8 illustrates the botryococcene synthase enzyme assay.

Typical BBS enzyme assays were initiated by mixing aliquots of 5 µl of E. coli lysate or purified BBS enzyme with 50 mM Tris, pH 7.0, 10 mM MgCl 5 mM-mercaptoethanol 4 M [3H]-FPP (1,800, dpm/pmole), plus as indicated 2 mM NADPH and 5 µl of lysate prepared from cells according to Okada et al. (2004) in 50 l total volume. Reactions were incubated at 37° C. for 1 h, then extracted with 100 µl hexane. Forty µl of the hexane extract was then spotted onto silica TLC plates with authentic standards of botryococcene and squalene, developed with hexane, and the standards visualized with iodine vapors. The TLC zones corresponding to squalene and botryococcene were scrapped and analyzed by scintillation spectrometry (see assay illustration, FIG. 8). After incubating lysates or purified BBS enzyme prepared from E. coli over-expressing the BBS cDNA with radiolabeled FPP, plus and minus reducing equivalents (NADPH) and algal lysates, the reaction products were separated by TLC prior to determining the amount of radioactivity incorporated in squalene (control) and botryococcene.

Figure 9:
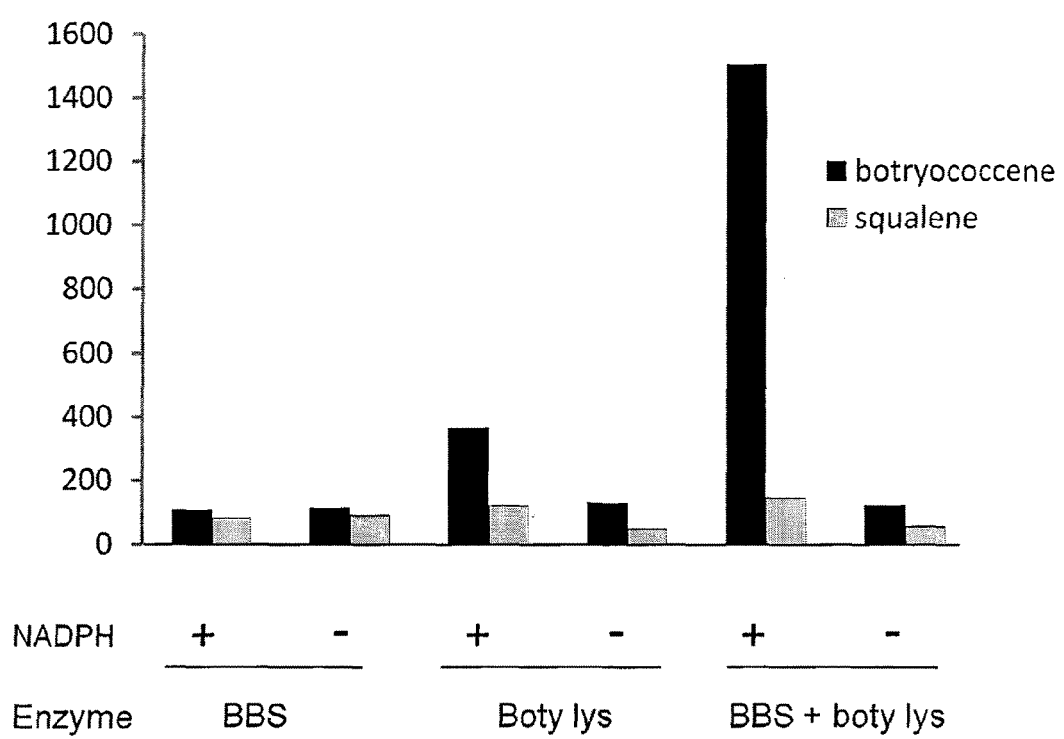
FIG. 9 depicts the enzyme activity of purified BBS protein, activity associated with a *B. braunii* lysate (boty lys), and BBS combined with lysate (BBS+boty lys) with or without NADPH. BBS containing an N-terminal hexa-histidine tag (SEQ ID NO: 44)_was expressed in *E. coli* and purified from bacterial lysate by nickel affinity chromatography according to the manufacturer (Novagen) (see FIG. 7).

*Botryococcus* lysate was prepared as described by Okada et al., (2004) and enzyme assays were performed with the components indicated in FIG. 9, then incubated at 37° C. for 1 h, and reaction products were then extracted with hexane. Aliquots of the hexane extracts was separated by silica TLC and the radioactivity migrating to zones corresponding to authentic standards of botryococcene and squalene determined by scintillation spectrometry. As shown in FIG. 9, incubation of the purified BBS enzyme with FPP, plus or minus the inclusion of NADPH, resulted in little, if any, botryococcene being formed. Similar low levels of background activity were observed in control incubations without any BBS enzyme being added. Botryococcene biosynthesis was evident at a very low level in incubations of the lysate, as was reported by Okada et al. (2004) earlier, but was dependent upon the addition of NADPH to the reaction mixture. However, a 5 to 10 fold stimulation of botryococcene biosynthesis was observed when the purified BBS enzyme was incubated with the lysate (FIG. 9). This botryococcene synthase activity was dependent upon the addition of NADPH, was equally supported by the additional of NADH, was time dependent with maximal activity observed after 1 hr incubation, and suggested that the BBS required an accessory or complementary factor found in the algal lysate for full enzyme activity.

Additional experiments demonstrated that the BBS enzyme was essential to the formation of botryococcene in these assays. Incubation of the purified BBS enzyme at 95° C. for 5 min prior to the enzyme assays eliminated all apparent botryococcene biosynthesis. Pre-treatment of the lysate with proteinase K, likewise abolished the botryococcene biosynthetic activity.

Altogether, the experimental data suggest that the BBS enzyme was not sufficient for botryococcene biosynthesis by itself and that an additional partner factor, perhaps an accessory protein (as suggested by the proteinase K sensitivity) as provided by the algal lysate, was necessary to observe the full complement of enzyme activity. Additional evidence for this suggestion was provided by over-expression of the BBS gene in yeast.

Example 3

Over Expression of the BBS Enzyme in Yeast

A yeast line, CALI-7, generates high intracellular concentrations of FPP. (Takahashi et al., (2007) "Biotech. Bioeng. 170-181). One further modification was introduced into this yeast line i.e., an insertional mutation in the ERG 1 gene. The ERG 1 gene of yeast encodes for the enzyme squalene epoxidase (Andrositz et al. (1991) Gene 155-60), which converts squalene to an epoxide form. The insertional mutation of this gene was created by introducing the TRP1 gene flanked by DNA sequences of the 5' and 3' region of the ERG 1 gene into the CALI-7 cells and subsequent selection for tryptophan auxotrophic growth according to the method of Wang et al. (2004) *Methods* 199-205. This modified yeast line is capable of accumulating high levels of FPP (Song, (2003) *Anal. Biochem.* 180-1 85), but not metabolizing squalene was denoted as TN7.

The BBS gene was then inserted into a standard yeast expression vector pYEP352 harboring an ADH1 promoter (Takahashi et al., 2007). This was accomplished by PCR amplification of the BBS gene with oligo nucleotide primers (5' CCGGAATTCAAAACAATGACTATGCACCAAGA CCACGG SEQ ID No. 42, EcoR1 restriction site in bold, 5' CCCAAGCTTCACTTGGTGGGAGTTGGGGCTGCGC SEQ ID No. 43, HindIII restriction site in bold) that introduced unique restriction enzyme sites at the 5' and 3' ends of the amplification product, digestion of the PCR amplification product with EcoR1 and HindIII restriction enzymes, followed by ligation of the isolated BBS DNA fragment into the pYEP352 vector digested with corresponding enzymes. The recombinant yeast expression vector was designated as pYEP-BBS and was introduced into the TN7 yeast line via lithium acetate transformation (Takahashi et al., 2007), followed by selection for uracil auxotrophic growth. A yeast line confirmed to possess the pYEP-BBS expression vector was identified by colony PCR and designated as TN7-BBS.

Individual colonies of TN7 and TN7-BBS were subsequently grown in 25 ml of YPDE media for 8 days at room temperature before analyzing the cultures for production of novel triterpene components (FIG. 10) In brief, 1 ml aliquots of the culture were combined with 1 ml of acetone, vigorously mixed, and incubated at room temperature for 3 min. One ml of hexane was added and mixed vigorously for 60 seconds. The mixture was then centrifuged briefly at 100 g to separate the phases, and the organic phase removed and concentrated to dryness under a nitrogen stream. The dried extract was resuspended in 50 µl of hexane and a 1 µl aliquot injected into a Thermo-Finnigan GC-MS. Compounds were separated on a Restek Rtx-5 (30 m by 0.25 µm) column with a initial temperature of 200° C. for 1 min, followed by an increase to 280° C. at 4° C./min, then to 320° C. with a 20° C./min ramp and a final 5 min hold at 320° C. Mass spectra were recorded in a DSQ quadrapole with the ionization set at 70 eV.

Figure 10:
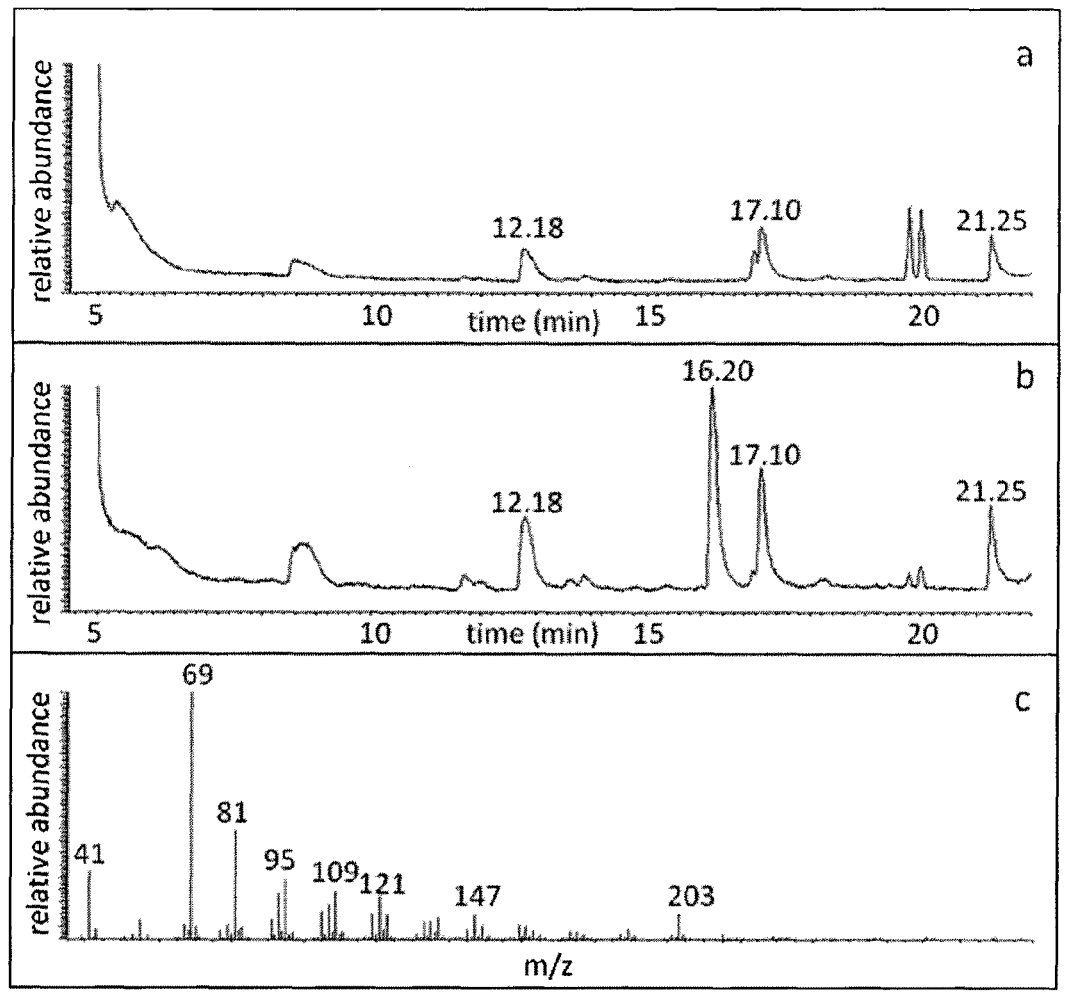
FIG. 10 depicts GC chromatographs of hexane extracts prepared from TN7 yeast (a) and TN7 yeast expressing BBS (b). The mass spectrum for the unique peak found in the TN7-BBS culture with a retention time of 16.20 is shown in panel c. The mass spectrum matches that of presqualene alcohol (PSOH) as described by Edmond et al. (1971) *J. Biol. Chem.* 6254-6251.

Comparison of the compounds accumulating specifically in the TN7-BBS lines and not in the TN7 lines identified pre-squalene alcohol, the dephosphorylated product of PSPP, as the only unique compound correlated with expression of the BBS gene (FIG. 10). This is consistent with the observation that additional factors provided by the lysate are necessary for the BBS enzyme to convert FPP to PSPP and then onto to the final product of botryococcene.

Example 4

Figure 11:
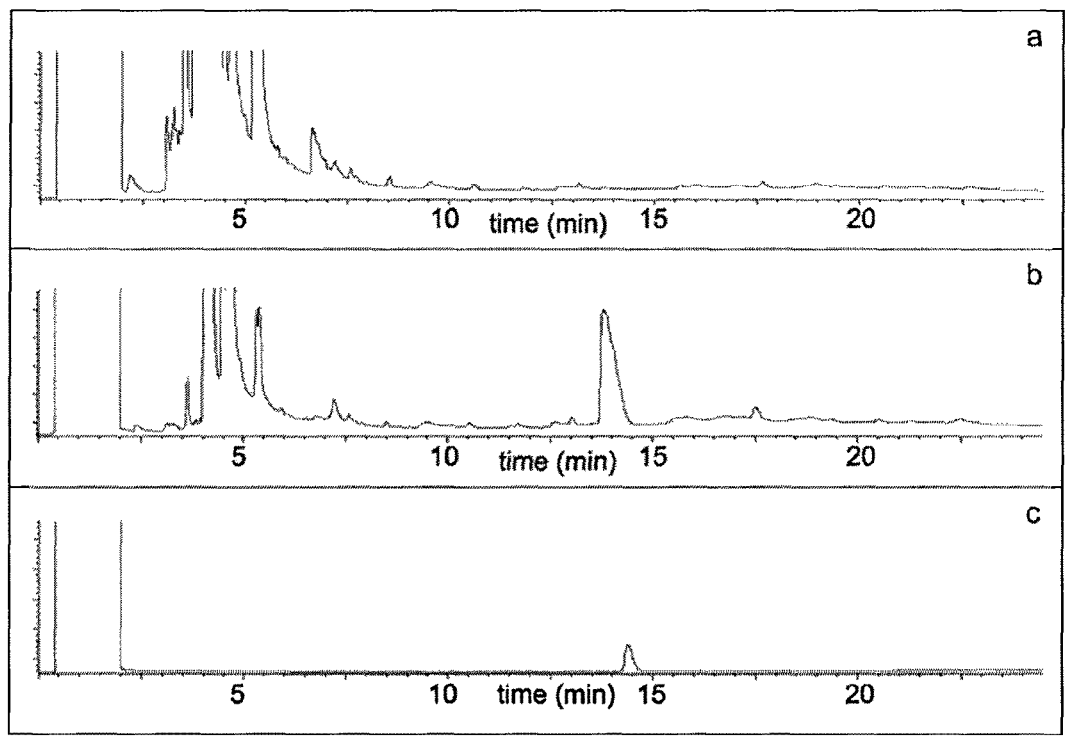
FIG. 11 depicts GC chromatographs of hexane extracts prepared from TN7 yeast (a) and TN7 yeast expressing a full length *B. braunii* squalene synthase gene (b). Identification of the novel compound accumulating in TN7 yeast expressing the squalene synthase gene (corresponding to the peak with retention time of approximately 14) was based on mass spectral comparisons (not shown) and identical chromatographic behavior of an authentic squalene (25 ng) standard (c).
Figure 12:
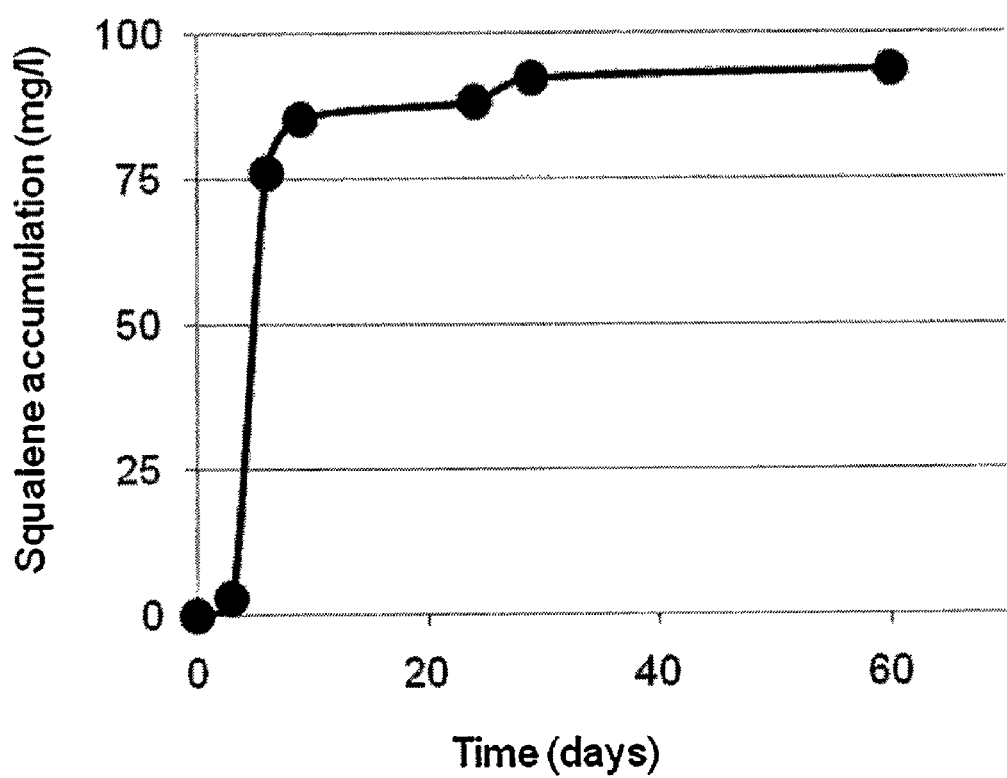
FIG. 12 depicts the accumulation of squalene in TN7 yeast over-expressing a *Botryococcus braunii* squalene synthase gene.

Accumulation of Squalene in TN7 Yeast Over-Expressing a *B. Braunii* Squalene Synthase Gene A yeast TN7 harboring the expression vector YEpD60 containing a squalene synthase gene was produced by transfecting TN7 with DNA sequence encoding the *B. braunii* squalene synthase gene as described by Okada et al. (2002). Recombinant yeast, verified by colony PCR for the plasmid, were grown in defined media and aliquots of the cell culture collected at the indicated times. For squalene determination, equal volumes of acetone were added to the cell culture samples, vortexed, incubated 15 min, then exacted with 2 volumes of hexane. The collected hexane was passed over a silica column and flow-through analyzed by GC as described above. The accumulation of squalene in TN7 yeast is shown in FIGS. 11 and 12.

We claim:
1. An isolated polypeptide having triterpene synthase activity wherein the polypeptide comprises peptide domains I, II, III, IV, and V; and
wherein:
domain I comprises the amino acid sequence of (SEQ ID NO: 3);
domain II comprises the amino acid sequence of (SEQ ID NO: 4;
domain III comprises the amino acid sequence of (SEQ ID NO: 5);
domain IV comprises the amino acid sequence of (SEQ ID NO 6); and
domain V comprises the amino acid sequence of (SEQ ID NO: 7).
2. The isolated polypeptide of claim 1, wherein:
(a) domain I is at least 95% identical to the amino acid sequence of SEQ ID NO: 3;
(b) domain II is at least 95% identical to the amino acid sequence of SEQ ID NO: 4;
(c) domain III is at least 95% identical to the amino acid sequence of SEQ ID NO: 5;
(d) domain IV is at least 95% identical to the amino acid sequence of SEQ ID NO: 6and
(e) domain Vis at least 95% identical to the amino acid sequence of SEQ ID NO: 7.
3. The isolated polypeptide of claim 1, which is a *Botryococcus braunii* triterpene synthase.
4. The isolated polypeptide of claim 1, which comprises the amino acid sequence of SEQ ID NO:2.
5. The isolated polypeptide of claim 1, which comprises at least 95% sequence identity to the amino acid sequence of SEQ ID NO:2.
6. An isolated polypeptide that comprises the amino acid sequence of SEQ ID NO:2, wherein said polypeptide has triterpene synthase activity.

* * * * *

SEQUENCE LISTING

<160> NUMBER OF SEQ ID NOS: 44

<210> SEQ ID NO 1
<211> LENGTH: 1209
<212> TYPE: DNA
<213> ORGANISM: Artificial Sequence
<220> FEATURE:

<223> OTHER INFORMATION: Description of Artificial Sequence: Synthetic
       polynucleotide

<400> SEQUENCE: 1

```
atgatgacta tgcaccaaga ccacggagtc atgaaagacc ttgtcaagca tccaaatgaa      60
tttccatact tgctccaact agctgcaaca tacggctcac cggctgcacc gatccccaag     120
gaaccggacc gagcttcctg ctacaatact cttcacaccg tttcgaaggg gttccccttt     180
gttatgagac ttccgcagga actccaagat ccgatatgca tattctacct cctgttgcga     240
gcactagaca cggtggagga tgatatgaac ctcaaaagtg agacgaagat ttcactccta     300
cgcgtttttcc atgaacactg ttcagacagg aactggagta tgaaaagtga ttatggcata     360
tatgcagatc tgatggaaag attcccccctg gtcgtatccg tcttagagaa gctccctccc     420
gccacacagc agactttcag ggagaatgtc aaatacatgg gcaatggcat ggcagatttt     480
attgataagc agatcctgac agtggatgag tacgacctct actgccacta tgtggccggc     540
agttgcggca ttgctgtcac caaggtcatt gtgcagttca accttgccac gcctgaagct     600
gactcctacg acttttccaa cagtctgggc ctcttgcttc agaaggccaa catcatcact     660
gactacaatg aagacatcaa tgaagagccc aggcccagga tgttctggcc ccaggagatt     720
tgggggaagt acgcggagaa gttggctgac ttcaatgaac ccgaaaatat tgatacagcc     780
gtgaagtgct tgaaccacat ggtcacagat gcaatgcggc acattgagcc ttccctcaaa     840
ggcatggttt atttcacaga caagacagtc tttcgggcgc tcgctcttct gctggtcaca     900
gcctttggcc atttgtccac tttgtacaac aaccccaatg tctttaaaga gaaagtgaga     960
cagcggaagg gaaggattgc acggctggtc atgtcatcca ggaatgtacc aggcctcttc    1020
cgtacatgcc tcaaactcgc aaacaacttc gagtccaggt gcaagcaaga gacggcaaat    1080
gatcccactg tggccatgac tatcaagcgc ttgcaatcta ttcaagctac atgcagagat    1140
ggcctggcca gtatgacaca ccctctggg ctgaaatctt tctgcgcagc cccaactccc    1200
accaagtga                                                             1209
```

<210> SEQ ID NO 2
<211> LENGTH: 401
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 2

```
Met Thr Met His Gln Asp His Gly Val Met Lys Asp Leu Val Lys His
1               5                   10                  15

Pro Asn Glu Phe Pro Tyr Leu Leu Gln Leu Ala Ala Thr Tyr Gly Ser
            20                  25                  30

Pro Ala Ala Pro Ile Pro Lys Glu Pro Asp Arg Ala Phe Cys Tyr Asn
        35                  40                  45

Thr Leu His Thr Val Ser Lys Gly Phe Pro Phe Val Met Arg Leu Pro
    50                  55                  60

Gln Glu Leu Gln Asp Pro Ile Cys Ile Phe Tyr Leu Leu Leu Arg Ala
65                  70                  75                  80

Leu Asp Thr Val Glu Asp Asp Met Asn Leu Lys Ser Glu Thr Lys Ile
                85                  90                  95

Ser Leu Leu Arg Val Phe His Glu His Cys Ser Asp Arg Asn Trp Ser
            100                 105                 110

Met Lys Ser Asp Tyr Gly Ile Tyr Ala Asp Leu Met Glu Arg Phe Pro
```

```
                    115                 120                 125
Leu Val Val Ser Val Leu Glu Lys Leu Pro Ala Thr Gln Gln Thr
    130                 135                 140
Phe Arg Glu Asn Val Lys Tyr Met Gly Asn Gly Met Ala Asp Phe Ile
145                 150                 155                 160
Asp Lys Gln Ile Leu Thr Val Asp Glu Tyr Asp Leu Tyr Cys His Tyr
                165                 170                 175
Val Ala Gly Ser Cys Gly Ile Ala Val Thr Lys Val Ile Val Gln Phe
            180                 185                 190
Asn Leu Ala Thr Pro Glu Ala Asp Ser Tyr Asp Phe Ser Asn Ser Leu
        195                 200                 205
Gly Leu Leu Leu Gln Lys Ala Asn Ile Ile Thr Asp Tyr Asn Glu Asp
    210                 215                 220
Ile Asn Glu Glu Pro Arg Pro Arg Met Phe Trp Pro Gln Glu Ile Trp
225                 230                 235                 240
Gly Lys Tyr Ala Glu Lys Leu Ala Asp Phe Asn Glu Pro Glu Asn Ile
                245                 250                 255
Asp Thr Ala Val Lys Cys Leu Asn His Met Val Thr Asp Ala Met Arg
            260                 265                 270
His Ile Glu Pro Ser Leu Lys Gly Met Val Tyr Phe Thr Asp Lys Thr
        275                 280                 285
Val Phe Arg Ala Leu Ala Leu Leu Val Thr Ala Phe Gly His Leu
    290                 295                 300
Ser Thr Leu Tyr Asn Asn Pro Asn Val Phe Lys Glu Lys Val Arg Gln
305                 310                 315                 320
Arg Lys Gly Arg Ile Ala Arg Leu Val Met Ser Ser Arg Asn Val Pro
                325                 330                 335
Gly Leu Phe Arg Thr Cys Leu Lys Leu Ala Asn Asn Phe Glu Ser Arg
            340                 345                 350
Cys Lys Gln Glu Thr Ala Asn Asp Pro Thr Val Ala Met Thr Ile Lys
        355                 360                 365
Arg Leu Gln Ser Ile Gln Ala Thr Cys Arg Asp Gly Leu Ala Lys Tyr
    370                 375                 380
Asp Thr Pro Ser Gly Leu Lys Ser Phe Cys Ala Ala Pro Thr Pro Thr
385                 390                 395                 400
Lys

<210> SEQ ID NO 3
<211> LENGTH: 14
<212> TYPE: PRT
<213> ORGANISM: Botryococcus braunii

<400> SEQUENCE: 3

Leu Pro Gln Glu Leu Gln Asp Pro Ile Cys Ile Phe Tyr Leu
1               5                   10

<210> SEQ ID NO 4
<211> LENGTH: 18
<212> TYPE: PRT
<213> ORGANISM: Botryococcus braunii

<400> SEQUENCE: 4

Leu Arg Ala Leu Asp Thr Val Glu Asp Asp Met Asn Leu Lys Ser Glu
1               5                   10                  15

Thr Lys
```

```
<210> SEQ ID NO 5
<211> LENGTH: 18
<212> TYPE: PRT
<213> ORGANISM: Botryococcus braunii

<400> SEQUENCE: 5

Tyr Cys His Tyr Val Ala Gly Ser Cys Gly Ile Ala Val Thr Lys Val
1               5                   10                  15

Ile Val

<210> SEQ ID NO 6
<211> LENGTH: 16
<212> TYPE: PRT
<213> ORGANISM: Botryococcus braunii

<400> SEQUENCE: 6

Gly Leu Leu Leu Gln Lys Ala Asn Ile Ile Thr Asp Tyr Asn Glu Asp
1               5                   10                  15

<210> SEQ ID NO 7
<211> LENGTH: 14
<212> TYPE: PRT
<213> ORGANISM: Botryococcus braunii

<400> SEQUENCE: 7

Ala Leu Ala Leu Leu Val Thr Ala Phe Gly His Leu Ser
1               5                   10

<210> SEQ ID NO 8
<211> LENGTH: 14
<212> TYPE: PRT
<213> ORGANISM: Botryococcus braunii

<400> SEQUENCE: 8

Leu Pro Ala Gln Leu Arg Asp Pro Val Cys Ile Phe Tyr Leu
1               5                   10

<210> SEQ ID NO 9
<211> LENGTH: 18
<212> TYPE: PRT
<213> ORGANISM: Botryococcus braunii

<400> SEQUENCE: 9

Leu Arg Ala Leu Asp Thr Val Glu Asp Asp Met Lys Ile Ala Ala Thr
1               5                   10                  15

Thr Lys

<210> SEQ ID NO 10
<211> LENGTH: 18
<212> TYPE: PRT
<213> ORGANISM: Botryococcus braunii

<400> SEQUENCE: 10

Tyr Cys His Tyr Val Ala Gly Val Val Gly Leu Gly Leu Ser Gln Leu
1               5                   10                  15

Phe Val

<210> SEQ ID NO 11
<211> LENGTH: 16
<212> TYPE: PRT
<213> ORGANISM: Botryococcus braunii

<400> SEQUENCE: 11

Gly Leu Phe Leu Gln Lys Thr Asn Ile Ile Arg Asp Tyr Phe Glu Asp
```

<210> SEQ ID NO 12
<211> LENGTH: 14
<212> TYPE: PRT
<213> ORGANISM: Botryococcus braunii

<400> SEQUENCE: 12

Phe Cys Ala Ile Pro Gln Thr Met Ala Phe Gly Thr Leu Ser
1               5                   10

<210> SEQ ID NO 13
<211> LENGTH: 14
<212> TYPE: PRT
<213> ORGANISM: Nicotiana tabacum

<400> SEQUENCE: 13

Leu Pro Val Glu Leu Arg Asp Ala Val Cys Ile Phe Tyr Leu
1               5                   10

<210> SEQ ID NO 14
<211> LENGTH: 18
<212> TYPE: PRT
<213> ORGANISM: Nicotiana tabacum

<400> SEQUENCE: 14

Leu Arg Ala Leu Asp Thr Val Glu Asp Asp Thr Ser Ile Pro Thr Asp
1               5                   10                  15

Val Lys

<210> SEQ ID NO 15
<211> LENGTH: 18
<212> TYPE: PRT
<213> ORGANISM: Nicotiana tabacum

<400> SEQUENCE: 15

Tyr Cys His Tyr Val Ala Gly Leu Val Gly Leu Gly Leu Ser Lys Leu
1               5                   10                  15

Phe His

<210> SEQ ID NO 16
<211> LENGTH: 16
<212> TYPE: PRT
<213> ORGANISM: Nicotiana tabacum

<400> SEQUENCE: 16

Gly Leu Phe Leu Gln Lys Thr Asn Ile Ile Arg Asp Tyr Leu Glu Asp
1               5                   10                  15

<210> SEQ ID NO 17
<211> LENGTH: 14
<212> TYPE: PRT
<213> ORGANISM: Nicotiana tabacum

<400> SEQUENCE: 17

Phe Cys Ala Ile Pro Gln Val Met Ala Ile Gly Thr Leu Ala
1               5                   10

<210> SEQ ID NO 18
<211> LENGTH: 14
<212> TYPE: PRT
<213> ORGANISM: Arabidopsis thaliana

<400> SEQUENCE: 18

```
Leu Asn Thr Glu Leu Arg Asn Ala Val Cys Val Phe Tyr Leu
1               5                   10

<210> SEQ ID NO 19
<211> LENGTH: 18
<212> TYPE: PRT
<213> ORGANISM: Arabidopsis thaliana

<400> SEQUENCE: 19

Leu Arg Ala Leu Asp Thr Val Glu Asp Asp Thr Ser Ile Pro Thr Asp
1               5                   10                  15

Glu Lys

<210> SEQ ID NO 20
<211> LENGTH: 18
<212> TYPE: PRT
<213> ORGANISM: Arabidopsis thaliana

<400> SEQUENCE: 20

Tyr Cys His Tyr Val Ala Gly Leu Val Gly Leu Gly Leu Ser Lys Leu
1               5                   10                  15

Phe Leu

<210> SEQ ID NO 21
<211> LENGTH: 16
<212> TYPE: PRT
<213> ORGANISM: Arabidopsis thaliana

<400> SEQUENCE: 21

Gly Leu Phe Leu Gln Lys Thr Asn Ile Ile Arg Asp Tyr Leu Glu Asp
1               5                   10                  15

<210> SEQ ID NO 22
<211> LENGTH: 14
<212> TYPE: PRT
<213> ORGANISM: Arabidopsis thaliana

<400> SEQUENCE: 22

Phe Cys Ala Ile Pro Gln Ile Met Ala Ile Gly Thr Leu Ala
1               5                   10

<210> SEQ ID NO 23
<211> LENGTH: 14
<212> TYPE: PRT
<213> ORGANISM: Zea mays

<400> SEQUENCE: 23

Leu Gly Pro Glu Leu Arg Asn Ala Val Cys Ile Phe Tyr Leu
1               5                   10

<210> SEQ ID NO 24
<211> LENGTH: 18
<212> TYPE: PRT
<213> ORGANISM: Zea mays

<400> SEQUENCE: 24

Leu Arg Ala Leu Asp Thr Val Glu Asp Asp Thr Ser Ile Pro Thr Glu
1               5                   10                  15

Val Lys

<210> SEQ ID NO 25
<211> LENGTH: 18
<212> TYPE: PRT
<213> ORGANISM: Zea mays
```

```
<400> SEQUENCE: 25

Tyr Cys His Tyr Val Ala Gly Leu Val Gly Tyr Gly Leu Ser Arg Leu
1               5                   10                  15

Phe Tyr

<210> SEQ ID NO 26
<211> LENGTH: 16
<212> TYPE: PRT
<213> ORGANISM: Zea mays

<400> SEQUENCE: 26

Gly Leu Phe Leu Gln Lys Thr Asn Ile Ile Arg Asp Tyr Leu Glu Asp
1               5                   10                  15

<210> SEQ ID NO 27
<211> LENGTH: 14
<212> TYPE: PRT
<213> ORGANISM: Zea mays

<400> SEQUENCE: 27

Phe Cys Ala Ile Pro Gln Ile Met Ala Ile Gly Thr Cys Ala
1               5                   10

<210> SEQ ID NO 28
<211> LENGTH: 14
<212> TYPE: PRT
<213> ORGANISM: Rattus rattus

<400> SEQUENCE: 28

Leu Asp Gly Asp Ile Arg His Ala Val Cys Val Phe Tyr Leu
1               5                   10

<210> SEQ ID NO 29
<211> LENGTH: 18
<212> TYPE: PRT
<213> ORGANISM: Rattus rattus

<400> SEQUENCE: 29

Leu Arg Ala Met Asp Thr Val Glu Asp Asp Met Ala Ile Ser Val Glu
1               5                   10                  15

Lys Lys

<210> SEQ ID NO 30
<211> LENGTH: 18
<212> TYPE: PRT
<213> ORGANISM: Rattus rattus

<400> SEQUENCE: 30

Tyr Cys His Tyr Val Ala Gly Leu Val Gly Ile Gly Leu Ser Arg Leu
1               5                   10                  15

Phe Ser

<210> SEQ ID NO 31
<211> LENGTH: 16
<212> TYPE: PRT
<213> ORGANISM: Rattus rattus

<400> SEQUENCE: 31

Gly Leu Phe Leu Gln Lys Thr Asn Ile Ile Arg Asp Tyr Leu Glu Asp
1               5                   10                  15

<210> SEQ ID NO 32
```

-continued

<211> LENGTH: 14
<212> TYPE: PRT
<213> ORGANISM: Rattus rattus

<400> SEQUENCE: 32

Phe Cys Ala Ile Pro Gln Val Met Ala Ile Ala Thr Leu Ala
1               5                   10

<210> SEQ ID NO 33
<211> LENGTH: 14
<212> TYPE: PRT
<213> ORGANISM: Saccharomyces cerevisiae

<400> SEQUENCE: 33

Leu His Pro Glu Leu Arg Asn Cys Val Thr Leu Phe Tyr Leu
1               5                   10

<210> SEQ ID NO 34
<211> LENGTH: 18
<212> TYPE: PRT
<213> ORGANISM: Saccharomyces cerevisiae

<400> SEQUENCE: 34

Leu Arg Ala Leu Asp Thr Ile Glu Asp Asp Met Ser Ile Glu His Asp
1               5                   10                  15

Leu Lys

<210> SEQ ID NO 35
<211> LENGTH: 18
<212> TYPE: PRT
<213> ORGANISM: Saccharomyces cerevisiae

<400> SEQUENCE: 35

Tyr Cys His Tyr Val Ala Gly Leu Val Gly Asp Gly Leu Thr Arg Leu
1               5                   10                  15

Ile Val

<210> SEQ ID NO 36
<211> LENGTH: 16
<212> TYPE: PRT
<213> ORGANISM: Saccharomyces cerevisiae

<400> SEQUENCE: 36

Gly Leu Phe Leu Gln Lys Thr Asn Ile Ile Arg Asp Tyr Asn Glu Asp
1               5                   10                  15

<210> SEQ ID NO 37
<211> LENGTH: 14
<212> TYPE: PRT
<213> ORGANISM: Saccharomyces cerevisiae

<400> SEQUENCE: 37

Phe Cys Ala Ile Pro Gln Val Met Ala Ile Ala Thr Leu Ala
1               5                   10

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cccgccacac agcagacttt caggg                                    25

```
<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cctggatgac atgaccagcc gtgc                                          24

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ttggcgccta tgactatgca ccaagaccac gg                                 32

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gggggcgcct cacttggtgg gagttggggc tgcgc                              35

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccggaattca aaacaatgac tatgcaccaa gaccacgg                           38

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cccaagcttc acttggtggg agttggggct gcgc                               34

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 44

His His His His His His
1               5
```